(12) United States Patent
Beyaert et al.

(10) Patent No.: US 7,122,656 B2
(45) Date of Patent: Oct. 17, 2006

(54) SPLICE VARIANT OF MYD88 AND USES THEREOF

(75) Inventors: Rudi Beyaert, Zingem (BE); Sophie Janssens, Ghent (BE)

(73) Assignees: Vlaams Interuniversitair Instituut voor Biotechnologie VZW, Zwijnaarde (BE); Universiteit Gent, Ghent (BE)

( * ) Notice: Subject to any disclaimer, the term of this patent is extended or adjusted under 35 U.S.C. 154(b) by 4 days.

(21) Appl. No.: 10/888,288

(22) Filed: Jul. 9, 2004

(65) Prior Publication Data

US 2005/0181476 A1  Aug. 18, 2005

Related U.S. Application Data

(63) Continuation of application No. PCT/EP03/00381, filed on Jan. 10, 2003.

(30) Foreign Application Priority Data

Jan. 10, 2002 (EP) ................................. 02075068

(51) Int. Cl.
   *C07K 14/705* (2006.01)
   *C07K 16/28* (2006.01)
   *C07K 1/00* (2006.01)
   *C07H 21/04* (2006.01)
   *C12P 21/04* (2006.01)

(52) U.S. Cl. .................... 536/23.5; 435/69.1; 530/350; 530/351

(58) Field of Classification Search ...................... None
See application file for complete search history.

(56) References Cited

U.S. PATENT DOCUMENTS 4,186,183 A  1/1980  Steck et al.

| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,194,596 A * | 3/1993 | Tischer et al. ............... 530/399 |
| 5,212,295 A | 5/1993 | Cook |
| 5,350,836 A * | 9/1994 | Kopchick et al. ........... 530/399 |
| 5,545,806 A | 8/1996 | Lonberg et al. |

(Continued)

FOREIGN PATENT DOCUMENTS

WO  WO 84/03564  9/1984

(Continued)

OTHER PUBLICATIONS

Benjamin et al., 1998, Development 125:1591-1598.*

(Continued)

*Primary Examiner*—Brenda Brumback
*Assistant Examiner*—Cherie M. Woodward
(74) *Attorney, Agent, or Firm*—TraskBritt

(57) ABSTRACT

The present invention relates to the field of infection and inflammation and, more specifically, to the field of pathogen-induced nuclear factor kappa B activation. More specifically, a novel splice variant of MyD88, (MyD88$_S$), which has been identified encoding a protein that inhibits LPS-induced NF-κB activation. MyD88$_S$ is a target to inhibit the phenomenon of endotoxin-tolerance that occurs in sepsis.

4 Claims, 7 Drawing Sheets

U.S. PATENT DOCUMENTS

| | | |
|---|---|---|
| 5,587,361 A | 12/1996 | Cook et al. |
| 5,599,797 A | 2/1997 | Cook et al. |
| 2002/0016460 A1 | 2/2002 | Snow et al. |

FOREIGN PATENT DOCUMENTS

| | | |
|---|---|---|
| WO | WO 91/16024 | 10/1991 |
| WO | WO 91/17424 | 11/1991 |
| WO | WO 93/24641 | 12/1993 |
| WO | WO 94/01131 | 1/1994 |
| WO | WO 94/04678 | 3/1994 |
| WO | WO 94/25591 | 11/1994 |
| WO | WO 94/26877 | 11/1994 |
| WO | WO 97/49805 | 12/1997 |
| WO | WO 99/60846 | 12/1999 |
| WO | WO 01/88137 | 11/2001 |
| WO | WO 03/057728 | 7/2003 |

OTHER PUBLICATIONS

Vukicevic et al. 1996, PNAS USA 93:9021-9026.*
Massague, 1987, Cell 49:437-8.*
Pilbeam et al., 1993, Bone 14:717-720.*
Skolnick et al. 2000, Trends in Biotech. 18:34-39.*
Bork. 2000, Genome Research 10:398-400.*
Doerks et al. 1998, Trends in Genetics 14:248-250.*
Smith et al. 1997, Nature Biotechnology 15:1222-1223.*
Brenner. 1999, Trends in Genetics 15:132-133.*
Bork et al. 1996, Trends in Genetics 12:425-427.*
Janssens et al. Curr Biol. Mar. 19, 2002 12:467-471.*
PCT International Search Report, PCT/EP03/00381, dated May 8, 2003.
PCT International Preliminary Examination Report, PCT/EP03/00381, date Apr. 1, 2004.
Janssens et al., "Identification and characterization of a splice variant of MyD88," Scandinavian Journal of Immunology, Jun. 2000, pp. 69, vol. 51, No. Supplement I.
Medzhitov et al., "MyD88 Is an Adaptor Protein in the hToll/IL-1 Receptor Family Signaling Pathways," Molecular Cell, Aug. 1998, pp. 253-258, vol. 2, No. 2.
Bonnert et al., "The cloning and characterization of human MyD88: a member of an IL-1 receptor related family," FEBS Letters, 1997, pp. 81-84, vol. 402, No. 1.
Byrd-Leifer et al., "The role of MyD88 and TRL4 in the LPS-mimetic activity of Taxol," European Journal of Immunology, Aug. 2001, pp. 2448-2457, vol. 31, No. 8.
Takeda et al., "Roles of Toll-like receptors in innate immune responses," Genes to Cells, Sep. 2001, pp. 733-742, vol. 6, No. 9.
Janssens et al., "Regulation of Interleukin-1- and Lipopolysaccharide-Induced NF-kappaB Activation by Alternative Splicing of MyD88," Current Biology, Mar. 19, 2002, pp. 467-471, vol. 12, No. 6.

* cited by examiner (a)

(b)

(c)

(a)

(b)

(c)

US 7,122,656 B2

SPLICE VARIANT OF MYD88 AND USES THEREOF

CROSS-REFERENCE TO RELATED APPLICATION

This application is a continuation of PCT International Application Number PCT/EP03/00381, filed on Jan. 10, 2003, designating the United States, and published as International Publication No. WO 03/057728 A1, in English, on Jul. 17, 2003, the contents of the entirety of which are incorporated by this reference.

TECHNICAL FIELD

The present invention relates generally to biotechnology, and more specifically to the field of infection and inflammation and, more specifically, to the field of pathogen-induced nuclear factor kappa B activation. More specifically, a novel splice variant of MyD88, (MyD88$_S$), has been identified encoding a protein that inhibits TLR-induced NF-κB activation. MyD88$_S$ is a target to inhibit the phenomenon of endotoxin-tolerance that occurs in sepsis.

BACKGROUND

The MyD88 gene was originally described as one of several myeloid differentiation primary response genes that are induced in murine M1 myeloblastic leukemia cells upon stimulation with IL-6. It is an exclusively cytosolic protein that functions as a unique adaptor for members of the type I interleukin-1 receptor (IL-1R)/Toll like receptor (TLR) family. The MyD88 protein has a modular structure. At its N-terminus, it has a "death domain" (DD) similar to the cytoplasmic signaling domains found in many members of the tumor necrosis factor (TNF) receptor superfamily. Its C-terminal domain is conserved in all members of the TLR/IL-1R super family and is, therefore, termed the "Toll/IL-1R" (TIR) domain. Both domains are required for MyD88 homodimerization and are separated by a short intermediate domain (ID) of unknown function. The TIR domain of MyD88 forms a homophilic interaction with the TIR domain of IL-1R and IL-1 Receptor accessory protein (IL-IRacP), IL-18R, and several TLRs, whereas the DD binds with the DD of both IL-1 receptor associated kinase (IRAK) and IRAK-2. Interaction with MyD88 triggers IRAK phosphorylation. Phosphorylated IRAK leaves the receptor complex and associates with TNF receptor-associated factor 6 (TRAF 6), which forms a molecular link to activation of NF-κB and c-jun N-terminal kinase (JNK). Targeted disruption of the MyD88 gene showed unamnbiguously the importance of MyD88 in IL-1, IL-18 and TLR (including LPS) signaling pathways. All IL-1 and IL-18 responses (including T-cell proliferation and induction of cytokines and acute phase proteins) were abrogated in MyD88$^{-/-}$ cells and no NF-κB or JNK activity was observed. MyD88$^{-/-}$ cells were resistant to LPS-induced endotoxic shock, but still showed delayed NF-κB translocation to the nucleus, which suggests redundancy at the level of MyD88 in the LPS-pathway.

MyD88 mRNA expression has been found to be constitutively expressed in many adult human tissues as a 2.6 kb mRNA species. In the present invention, we describe the identification, characterization and uses of a splice variant of MyD88, termed MyD88$_S$, which encodes for a protein lacking the ID. We have disclosed earlier the occurrence of an unknown splice variant of MyD88, lacking part of the TIR domain, that can inhibit IL1-induced NF-κB activation (Janssens S. and Beyaert R. (2000) *Scandinavian J. of Immunology*, 51 (Suppl. 1), 1.

DISCLOSURE OF THE INVENTION

A first aspect of the invention deals with endotoxin tolerance. Endotoxin tolerance is thought to be an adaptive response to protect the body from hyper-activation of the innate immune system during bacterial infections. However, although preventing the initial development of sepsis, endotoxin tolerance can also lead to a fatal blunting of the immune response to subsequent infections in survivors of sepsis (Kox et al. (2000) *Intensive Care Med.* 26, 124). Despite considerable efforts to find therapies to treat patients fiom septic shock, so far most clinical trials yielded disappointing results (Kox et al. (2000) *Intensive Care Med.* 26, 124). Most of them were aimed at down-regulation of the hyper-inflammatory state by administration of IL-1 antagonists or anti-TNF or anti-LPS-antibodies. One of the reasons for the failure of these therapies might be the delay between the onset of sepsis and the beginning of treatment thus, at the time the patient enters the hospital, the initial hyper-inflammatory state is already counteracted by a secondary hypo-inflammatory response. Therefore, new therapies focus on a restoration of the immune response by treatment with pro-inflammatory molecules (Docke et al. (1997) *Nature Med.* 3(6) 678). However, restoration of the response might be hampered by cross-tolerance against IL-1 and TNF. Therefore, directly interfering with the development of tolerance is a more attractive approach. Endotoxin tolerance is associated with monocyte deactivation which results in an impaired cytokine production or HLA-DR expression. The situation can be mimicked in vitro by pretreatment of monocytes with endotoxin which makes them refractory to subsequent LPS challenges (Adib-Conquy et al. (2000) *Am. J. Respir. Crit. Care Med.* 164, 1877). Several mechanisms have been proposed to explain the impaired response, e.g., diminished expression of TLR, changed p65/p50 ratio or expression of immuno-inhibitory factors such as IL10. Recently, a paper by Li et al. ((2000) *J. Biol. Chem.* 275, 23340), shows that IRAK-phosphorylation upon LPS activation is impaired in endotoxin-tolerant monocytes. Here, we show that MyD88$_S$, a splice variant of MyD88 which blocks NF-κB activation, prevents IRAK-phosphorylation and is up-regulated in endotoxin-tolerant monocytes. The present invention shows that MyD88$_S$ has a role in the induction of endotoxin tolerance, the transient, secondary down-regulation of a subset of endotoxin-driven responses after exposure to bacterial products. It is shown that MyD88$_S$ behaves as a dominant negative inhibitor of LPS-, but not of TNF-induced NF-κB activation.

A second aspect of the invention deals with the so-called JNK and NF-κB signaling pathways, both of which consist of tiers of protein kinases and are pivotal in determining whether cells die or survive. The JNKs are part of the evolutionarily conserved mitogen-activated protein kinase family and are implicated in cell death pathways stimulated by environmental stresses and TNF. Once activated, JNK proteins can move from the cytoplasm of the cell into the nucleus. There, they phosphorylate and activate numerous transcription factors. However, the exact mechanism by which JNKs contribute to cell death are still unknown, but mostly cell death requires a sustained activation of the JNK pathway. In contrast, NF-κB enhances cell survival by switching on genes that dampen pro-apoptotic signals. It was shown that NF-κB can down-regulate pro-apoptotic JNK signaling in response to TNF and chemotherapeutic drugs by shifting the sustained JNK activation to a more transient activation. The JNK-inhibiting effect of NF-κB was mediated by the transcriptional up-regulation of specific proteins (XIAP, Gadd45β). The present invention demonstrates that MyD88$_S$ allows specific activation of the JNK pathway and AP-1-dependent gene expression, while blocking NF-κB-dependent gene expression. Since it is known that the c-JUN N-terminal kinase pathway is involved in the control of programmed cell death, MyD88$_S$ can be used to stimulate apoptosis in, for example, cancer or other situations where a lack of programmed cell death occurs.

A third aspect of the invention deals with the expression of MyD88$_S$ in immune privileged tissues. Immune privilege is an example of regional immunity: immune effector cells are not only differentiated for maximum ability to eliminate pathogens, but also for minimum ability to interfere with a specific organ or tissue's physiological function. It has been described in certain sites of the body (testis, eye, brain, placenta) which show a limited and controlled activation of the local immune response and has been associated with immunosuppression and increased programmed cell death of invading inflammatory cells (Streilein (1995) Science, 270, 1158; Ferguson and Griffith (1997) Immunol. Rev., 156, 167).

The present invention shows that MyD88$_S$ is specifically expressed in brain, testis, and eye of C57/BL6 mice, which is consistent with a role in immune privilege.

The present invention also shows expression of MyD88$_S$ in the spleen under specific conditions (e.g. in Balb/c mice; in TNF-treated C57/BL6 mice). The spleen has a well-established role in immune regulation. As a lymphoid organ, it provides a microenvironment where several immune cells come into close proximity, enabling a more efficient immune response (for review, see Delves and Roitt (2000) New EngL. J. Med. 343, 108). Besides having a role in the initiation of an immune reaction, a more immunoregulatory and immunosuppressive role has also been attributed to the spleen. In several situations such as graft-versus-host disease (Wall et al. (1988) J. Immunol., 140, 2970), cyclophosphamide treatment (Angulo et al. (2000) Blood, 95, 212), Vaccinia-virus infection (Bronte et al. (1998) J. Immunol., 161, 5313) or in tumor models (Kusmartsev et al. (2000) J. Immunol., 165, 779), an immune-suppressive cell population can be found in the spleen, accounting for the marked splenic B/T cell hypo-responsiveness occurring in these conditions. The exact nature of these so-called "natural suppressor" cells is far from clear and may be different in each model system, although most data suggest that the immunosuppressive activity can be attributed to non-lymphoid cells, derived from the monocyte/macrophage lineage (Bronte et al. (2000) Blood, 96, 3838). Therefore, MyD88$_S$ can be used to obtain immunosuppression (e.g., in the case of transplantation).

In conclusion, the invention shows that modulation of the expression of MyD88$_S$ can regulate the cellular responses to LPS and other immunological stimuli.

DETAILED DESCRIPTION OF THE INVENTION

Figure 1:
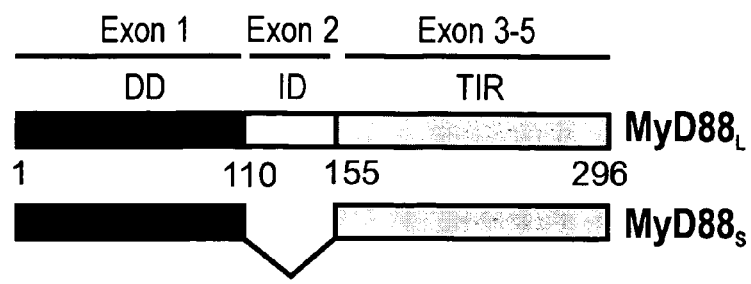
FIG. 1: Identification of a splice variant of MyD88, which lacks the intermediate domain. (a) Schematic representation of the MyD88$_L$ and MyD88$_S$ protein structure, showing the three different domains and the corresponding exons. Numbers refer to the positioning of the amino acids. (b) RT-PCR with MyD88 specific primers on RNA isolated from Mf4/4 cells. The second lane shows a control without reverse transcriptase (RT). (c) PCR analysis on a Balb/c mouse tissue cDNA panel with MyD88 and β-actin-specific primers.
Figure 1:
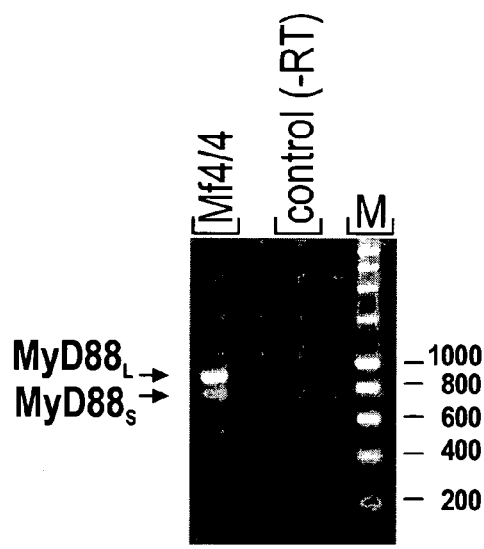
Figure 1:
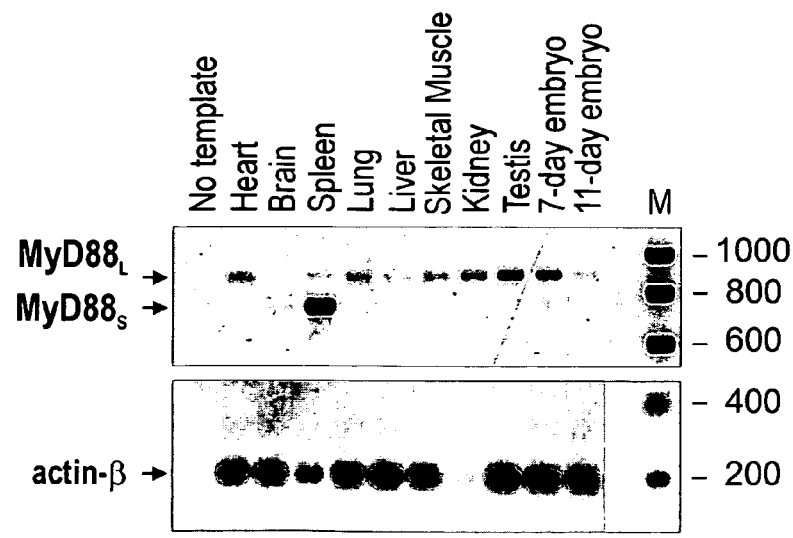

MyD88 is an adaptor protein that is involved in signaling triggered by various members of the interleukin-1 receptor (IL-1R)/Toll-like receptor (TLR) superfamily. A role for MyD88 has been shown in response to triggering of IL-1R, IL-18R, TLR2, TLR3, TLR4, TLR9. IL-1 and IL-18 are pleiotropic cytokines which play a central role in the immune response and in many inflammatory diseases such as rheumatoid arthritis or septic shock. TLRs behave as receptors for various microbial products (including bacterial, viral, yeast-derived products). Members of the IL-1R/TLR superfamily, as well as MyD88 have been shown to play an important role in both innate and adaptive immune responses.

In the present invention, we provide a splice variant of MyD88, MyD88$_S$, which lacks its intermediate domain, the domain in between the N-terminal death domain (necessary for interaction with IRAK) and the C-terminal TIR domain (necessary for interaction with the IL-1 R or TLR). Deletion of the intermediate domain abolishes the ability of MyD88$_S$ to activate NF-κB. In contrast, MyD88$_S$ acts as a dominant negative inhibitor of the IL-1- and LPS-induced signaling pathway to NF-κB by interfering at the level of IRAK phosphorylation. In contrast to full length MyD88, we show that MyD88$_S$ does not mediate phosphorylation of co-expressed IRAK. Because MyD88 is also essential for the activation of JNK in response to IL-1R and TLR triggering, we were interested to see if MyD88$_S$ still allows IL-1 induced JNK activation. We surprisingly found that MyD88$_S$ indeed allows activation of JNK and AP-1, whereas the NF-κB pathway is completely blocked.

In a first embodiment, the invention provides an isolated polypeptide, designated as the splice form MyD88$_S$, having the primary structural information of amino acids 1–251 as set forth in SEQ ID NO:2, or a homologue or functional fragment thereof, possessing the biological properties of (1) down-regulating the TLR-induced nuclear factor kappa B activation and (2) activating the c-JUN N-terminal kinase pathway.

In a particular embodiment, TLR functions as a receptor for lipopolysaccharide (LPS).

The wording "TLR-induced" or "Toll Like Receptor-induced" is further clarified. TLRs recognize so-called pathogen-associated molecular patterns or PAMPs. PAMPs are conserved motifs, unique to microorganisms and essential for their metabolism and, thus, survival. Up to now, ten different TLRs have been identified in humans, which mediate recognition of diverse classes of pathogens. It is now clear that one group of pathogens is not exclusively recognized by one TLR (e.g., both TLR2 and TLR4 recognize Gram-positive-derived PAMPs) and that one TLR can respond to many structurally unrelated ligands, which are often derived from different groups of pathogens (e.g., TLR4 recognizes both viral components as well as gram-negative LPS). In contrast, other TLRs, like TLR3, 5 and 9, seem to be more ligand-specific and at least up to now, appear to recognize only one type of ligand. Most TLR ligands identified so far are conserved microbial products which signal the presence of an infection. In addition, TLR7 and TLR8 have been shown to recognize synthetic anti-viral compounds with strong immunostimulatory capacity, belonging to the group of imidazoquinolines. The natural ligands of TLR7 and TLR8, however, remain to be identified. Finally, TLRs also recognize host-derived ligands such as the extra domain A of the extracellular matrix protein fibronectin or heat shock proteins. Extracellular matrix proteins are often proteolytically cleaved during infection to facilitate access of macrophages and other immune effector cells to the site of infection. The extra domain A (EDA) of fibronectin is encoded by an alternatively spliced exon, which is induced only upon tissue injury. Heat shock proteins are normally expressed in the cytoplasm, thus not available for recognition by cell-surface receptors, but can be released by necrotic cells during tissue injury or viral infection. In this way, fragments of fibronectin containing the EDA region or heat shock proteins alert TLRs for an abnormal situation, e.g. tissue injury. Activation of TLRs by endogenous ligands implies that they do not only distinguish between self and non-self, but rather sense the presence of "danger" which can be either non-self or harmful self. MyD88 proved to be essential for cytokine induction after stimulation with a variety of ligands such as IL-1β, IL-18, LPS, mycoplasmal macrophage-activating lipopeptide-2 (MALP-2), bacterial CpG DNA, poly(I:C) and many others. All these ligands have been demonstrated to signal through different receptors of the TLR/IL-1R superfamily, suggesting that MyD88 is a universal adaptor for the TLR/IL-1R superfamily. MALP-2 signals through TLR2, LPS through TLR4, Poly(I:C) double-stranded RNA through TLR3, CpG DNA through TLR9.

As used herein, "fragment" refers to a polypeptide or polynucleotide of at least about 9 amino acids or 27 base pairs, typically 50 to 75, or more amino acids or base pairs, wherein the polypeptide contains an amino acid core sequence. A fragment may be, for example, a truncated MyD88$_S$ isoform, modified MyD88$_S$ isoform (as by amino acid substitutions, deletions, or additions outside of the core sequence), or other variant polypeptide sequence, but is not a naturally occurring MyD88$_S$ isoform that is present in a human individual. If desired, the fragment may be fused at either terminus to additional amino acids or base pairs, which may number from 1 to 20, typically 50 to 100, but up to 250 to 500 or more.

A "functional fragment" means a polypeptide fragment of MyD88$_S$ possessing the biological properties described above or a polynucleotide fragment encoding the MyD88$_S$ polypeptide fragment possessing the biological properties described above. According to still further features in the described preferred embodiments, the polynucleotide sequence which encodes a polypeptide designated as MyD88$_S$ and has the biological properties of MyD88$_S$ and shares at least 60% homology, preferably at least 70% homology, more preferably at least 80% homology, and most preferably, at least 90% homology with SEQ ID NO:1. Homology is determined using default parameters of a DNA sequence analysis software package developed by the Genetic Computer Group (GCG) at the University of Wisconsin. Also forming part of the invention are allelic variants.

The wording "allelic variant" means any of two or more alternative forms of a gene occupying the same chromosomal locus. Allelic variation arises naturally through mutation and may result in phenotypic polymorphism within populations. Gene mutations can be silent (no change in the encoded polypeptide) or may encode polypeptides having altered amino acid sequence. The term allelic variant also means a protein encoded by an allelic variant of a gene.

The term "down-regulating the TLR-induced nuclear factor kappa B activation" means that MyD88$_S$ down-regulates the NF-κB activation, with respect to the cell which was activated with LPS or other TLR ligands, with at least 50%, 60%, 70%, 80% or preferentially with 90%, 95%, 99% or even 100%. The term "activating" in the wording "activating the c-JUN N-terminal kinase pathway" means that the c-JUN N-terminal kinase pathway is still active while the NF-κB-pathway is shut down.

The scientific relevance and background of the wording "activating the c-JUN N-terminal kinase pathway" is herein further explained.

It is known in the art that stimulation of IL-1R and TLR activates several intracellular signaling pathways that include the IκB kinase (IKK)-pathway and three mitogen-activated protein kinase (MAPK) pathways: extracellular signal-regulated kinases (ERK) 1 and 2, c-Jun N-terminal kinase (JNK) and p38. The IKK-pathway in turn activates the transcription factor NF-κB, whereas JNK activates several other transcription factors, including AP-1, Elk-1, NF-AT, ATF-2, as well as a number of other substrates (e.g. bcl-X$_L$) (Barr et al. (2001) *Int J. Biochem. Cell Biol.* 33:1047). The transcription factor AP-1 by phosphorylating the c-jun and ATF-2 component. Both NF-κB and AP-1 coordinate the induction of various genes encoding inflammatory mediators, anti-apoptotic proteins, and many others. Targeted gene knock-out studies have also demonstrated a role for JNK in T-cell activation, thymic development and Th1/Th2 differentiation. Recently, a link between the NF-κB and JNK pathways has been established. It was shown that NF-κB can down-regulate pro-apoptotic JNK signaling in response to TNF and chemotherapeutic drugs by shifting the sustained JNK activation to a more transient activation. The JNK-inhibiting effect of NF-κB was mediated by the transcriptional up-regulation of specific proteins (XIAP, Gadd45β).

Finally, JNK activation has also been implicated in cell death (e.g., excitotoxicity-induced apoptosis in the hippocampus; IL-1 induced cell death of pancreatic β-cells; death following cardiac ischemia-reperfusion; UV-induced apoptosis of small cell lung carcinoma; degenerating neurones in Alzheimer's disease). Interestingly, cell death has been correlated with a sustained JNK activation, whereas transient activation is not associated with cell death but, in contrast, might have a survival role (e.g., protection of myocytes from nitric oxide-induced apoptosis, protection of HeLa cells from apoptosis following photodynamic therapy) (Roulston et al. (1998) *J. Biol. Chem.* 273:10232; Assefa et al. (1999) *J. Biol. Chem.* 274:8766).

In another embodiment, the invention provides a polynucleotide encoding a polypeptide designated as the splice form MyD88$_S$, having the primary structural information of amino acids 1–251 as set forth in SEQ ID NO:2 or any homologue or functional fragment thereof, possessing the biological properties of (1) down-regulating the TLR-induced nuclear factor kappa B activation and (2) activating the c-JUN N-terminal kinase pathway. In a particular embodiment, TLR-induced nuclear factor kappa B activation is an LPS-induced nuclear factor kappa B activation.

As used herein, the words "polynucleotide" may be interpreted to mean the DNA and cDNA sequence as detailed by Yoshikai et al. (1990) *Gene* 87:257, with or without a promoter DNA sequence as described by Salbaum et al. (1988) *EMBO J.* 7(9):2807.

In a particular embodiment, the invention provides a polynucleotide as described hereinbefore as set forth in SEQ ID NO:1.

In yet another embodiment, the invention provides a molecule which comprises a region specifically binding to the intermediate domain of MyD88 or nucleic acids encoding the intermediate domain of MyD88, and modulates NF-κB activation and/or IRAK phosphorylation and/or activation of the c-JUN N-terminal kinase pathway. The term "modulates" can either mean activates (meaning also, for example, stimulates or enhances) or inhibits (meaning also, for example, down-regulates or suppresses).

In yet another embodiment, the invention provides a molecule which comprises a region specifically binding to the intermediate domain of MyD88 or nucleic acids encoding the intermediate domain of MyD88 and suppresses or prevents MyD88 expression but not MyD88$_S$ expression, and activates the c-JUN N-terminal kinase pathway and inhibits the TLR-mediated nuclear factor kappa B pathway.

In yet another embodiment, the molecule which comprises a region specifically binding to the intermediate domain of MyD88 or nucleic acids encoding the intermediate domain of MyD88 and suppresses or prevents MyD88 expression but not MyD88$_S$ expression, and activates the c-JUN N-terminal kinase pathway is chosen from the group comprising an antibody or any fragment thereof, a small molecule, a ribozyme, an oligonucleotide, a peptide or a peptidomimetic.

The term "antibody" or "antibodies" relates to an antibody characterized as being specifically directed against the intermediate domain of MyD88, with the antibodies being preferably monoclonal antibodies; or an antigen-binding fragment thereof, of the F(ab')$_2$, F(ab) or single chain Fv type, or any type of recombinant antibody derived thereof. These antibodies of the invention, including specific polyclonal antisera prepared against the intermediate domain of MyD88, have no cross-reactivity to other proteins. The monoclonal antibodies of the invention can, for instance, be produced by any hybridoma liable to be formed according to classical methods from splenic cells of an animal, particularly of a mouse or rat immunized against the intermediate domain of MyD88, and of cells of a myeloma cell line, and to be selected by the ability of the hybridoma to produce the monoclonal antibodies recognizing the intermediate domain of MyD88 which have been initially used for the immunization of the animals. The monoclonal antibodies, according to this embodiment of the invention, may be humanized versions of the mouse monoclonal antibodies made by means of recombinant DNA technology, departing from the mouse and/or human genomic DNA sequences coding for H and L chains or from cDNA clones coding for H and L chains. Alternatively, the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also, fragments derived from these monoclonal antibodies such as Fab, F(ab)'$_2$ and scFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type.

The antibody against the intermediate domain of MyD88 can also be camel antibody or a functional fragment thereof. Camel antibodies are fully described in WO 94/25591, WO 94/04678 and in WO 97/49805.

Processes are described in the art which make it possible that antibodies can be used to hit intracellular targets. Since the intermediate domain of MyD88 is such an intracellular target, the antibodies or fragments thereof with a specificity for the ID domain must be delivered into the cells. One such technology uses lipidation of the antibodies. The latter method is fully described in PCT International PubWO 94/01131, which is herein incorporated by reference.

Also within the scope of the invention are oligonucleotide sequences that include anti-sense RNA and DNA molecules and ribozymes that function to inhibit the translation of MyD88 but not the translation of MyD88$_S$. Anti-sense RNA and DNA molecules act to directly block the translation of the part of the mRNA that encode the intermediate domain of MyD88 by binding to the targeted mRNA and preventing protein translation. Ribozymes are enzymatic RNA molecules capable of catalyzing the specific cleavage of RNA. The mechanism of ribozyme action involves sequence specific hybridization of the ribozyme molecule to complementary target RNA, thus to the mRNA encoding the ID-domain of MyD88, followed by an endonucleolytic cleavage within this region.

Within the scope of the invention are engineered hammerhead motif ribozyme molecules that specifically and efficiently catalyze endonucleolytic cleavage within the intermediate domain sequence of MyD88. Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site (here the target being the intermediate domain of MyD88) may be evaluated for predicted structural features such as a secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, anti-sense cDNA constructs that synthesize anti-sense RNA constitutively or inducibly, depending on the promoter used, can be introduced stably into cell lines.

Beside the inhibition of translation, the anti-sense oligonucleotide sequences can work through the use of RNA inhibition (RNAi) with the invention herein applying anti-sense oligonucleotides that are specifically directed to the sequence that encodes the intermediate domain of MyD88 that is missing in MyD88$_S$ and forms a siRNA duplex. RNAi is based on the degradation of particular target sequences by the design of short interference RNA oligos (siRNA) which recognize the target sequence and subsequently trigger their degradation by a poorly understood pathway. The siRNA duplexes should be shorter than 30 nucleotides because longer stretches of dsRNA activate the PKR pathway in mammalian cells, which results in a global a-specific shutdown of protein synthesis. Target regions should be AA(N19)TT or AA(N21), should be specific for the gene of interest and should have a GC content of approximately 50%. The siRNAs duplexes can, for example, be transfected in the cells of interest by oligofectamin (Life Technologies) and the transfection efficiency reaches 90–95%.

In addition to inhibition of mRNA translation or inducing RNA interference, anti-sense oligonucleotides can also alter mRNA structure by modulating splicing of pre-mRNA. Oligonucleotide-induced alteration of splicing includes shifting of alternative splicing pathways, skipping of exons or inclusion of introns. Since splicing is a nuclear process, the anti-sense molecules must be active in the nuclei of the cells. It has been shown in the art how anti-sense oligonucleotides can be used to manipulate the splicing "equilibrium" and redirect alternative splicing routes (Kole R. and Sazani P. K (2001) Curr. Opinion Mol. Therapeutics 3, 229). An oligonucleotide targeted towards the 5' splice site competes, for example, with U1 snRNP thus decreasing its binding and driving the utilization of an alternative 5' splice site. Because of the predominance of alternative splicing, its gene-specific modification is of significant clinical interest.

In yet another embodiment, the invention provides a peptide or a peptidomimetic thereof which is derived from a region of MyD88, amino acids 95 to 172, depicted in SEQ ID NO:14. SEQ ID NO:14 comprises the ID domain of MyD88. The ID domain is depicted in SEQ ID NO:15 (which is defined as a region encompassing amino acids 110 to 154 of MyD88). Preferably, the peptide or peptidomimetic comprises at least 5, 10, 15, or 20 residues or more derived from the sequence depicted in SEQ ID NO:15. The wording "peptidomimetic" is described further. The term "peptidomimetic" means a molecule able to mimic the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics, according to this invention, provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide. The peptidomimetics of this invention are preferably substantially similar in both three-dimensional shape and biological activity to the peptides set forth above. "Substantial similarity" means that the geometric relationship of groups in the peptide that react with, for example, the ID region of MyD88 or SEQ ID NO:14 is preserved. There are clear advantages for using a mimetic of a given peptide rather than the peptide itself, because peptides commonly exhibit two undesirable properties: (1) poor bioavailability and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are much cheaper to produce than peptides. Finally, there are problems associated with stability, storage and immunoreactivity for peptides that are not experienced with peptide mimetics. The peptides described in the present invention have utility in the development of such small chemical compounds with similar biological activities and, therefore, with similar therapeutic utilities. The techniques of developing peptidomimetics are conventional. Thus, peptide bonds can be replaced by non-peptide bonds that allow the peptidomimetic to adopt a similar structure and, therefore, biological activity, to the original peptide. Further modifications can also be made by replacing chemical groups of the amino acids with other chemical groups of similar structure. The development of peptidomimetics can be aided by determining the tertiary structure of the original peptide, either free or bound to a substrate, e.g. the ID region of MyD88, by NMR spectroscopy, crystallography and/or computer-aided molecular modeling. These techniques aid in the development of novel compositions of higher potency and/or greater bioavailability and/or greater stability than the original peptide (Dean (1994), *BioEssays*, 16:683–687; Cohen and Shatzmiller (1993), *J. Mol. Graph.*, 11: 166–173; Wiley and Rich (1993), *Med. Res. Rev.*, 13: 327–384; Moore (1994), *Trends Pharmacol. Sci.*, 15: 124–129; Hruby (1993), *Biopolymers*, 33: 1073–1082; Bugg et al. (1993), *Sci. Am.*, 269: 92–98, all incorporated herein by reference). Once a potential peptidomimetic compound is identified, it may be synthesized and assayed using the method described herein to assess its activity. It will furthermore be apparent that the peptidomimetics of this invention can be further used for the development of even more potent non-peptidic compounds, in addition to their utility as therapeutic compounds.

In yet another embodiment, the invention provides a molecule which comprises a region specifically binding to nuclear pre-RNA encoding MyD88 or mRNA encoding MyD88$_S$, and suppresses or prevents MyD88$_S$ expression but not MyD88 expression, and inhibits the down-regulation of TLR-induced nuclear factor kappa B activation. In a particular embodiment the molecule is an oligonucleotide.

In another particular embodiment in the TLR-induced nuclear factor kappa B activation, TLR functions as a receptor for LPS.

In yet another embodiment, the invention provides a molecule which comprises a region specifically binding to nuclear pre-RNA encoding MyD88 or mRNA encoding MyD88$_S$ and induces or stimulates MyD88$_S$ expression but not MyD88 expression, and the down-regulation of TLR-induced nuclear factor kappa B activation, wherein the molecule is an oligonucleotide.

We have shown in this invention that there occurs a high expression of MyD88$_S$ in immune-privileged tissues. Indeed it is shown that MyD88$_S$ is specifically expressed in brain, testis, and eye of C57/BL6 mice, which is consistent with a role in immune privilege.

Therefore, in another embodiment, molecules able to modulate the expression of MyD88$_S$ can be used to modulate immunosuppression (e.g., in the case of transplantation, it is desired that there occurs a stimulation of immunosuppression).

As used herein, the term "oligonucleotide" is intended to include both naturally occurring and non-naturally occurring (i.e., "synthetic") oligomers of linked nucleosides. Although such linkages generally are between the 3' carbon of one nucleoside and the 5' carbon of a second nucleoside (i.e., 3'–5' linkages), other linkages (such as 2'–5' linkages) can be formed. Naturally occurring oligonucleotides are those which occur in nature; for example, ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild-type oligonucleotides. Thus, non-naturally occurring oligonucleotides include all such structures which function effectively to mimic the structure and/or function of a desired RNA or DNA strand, for example, by hybridizing to a target. Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, and 7-methylguanine. Further, naturally and non-naturally occurring nucleobases include those disclosed in U.S. Pat. No. 3,687,808 (Merigan, et al.); in chapter 15 by Sanghvi, in *Antisense Research and Application*, Ed. S. T. Crooke and B. Lebleu, CRC Press, 1993; in Englisch et al., *Angewandte Chemie*, International Edition, 1991, 30, 613–722 (see especially pages 622 and 623); and in the *Concise Encyclopedia of Polymer Science and Engineering*, J. I. Kroschwitz Ed., John Wiley & Sons, 1990, pages 858–859; Cook, *Anti-Cancer Drug Design* 1991, 6, 585–607; each of which are hereby incorporated by reference in their entirety.

The term "nucleosidic base" is further intended to include heterocyclic compounds that can serve as like nucleosidic bases, including certain "universal bases" that are not nucleosidic bases in the most classical sense but serve as nucleosidic bases. Especially mentioned as a universal base is 3-nitropyrrole. Sugars having O-substitutions on the ribosyl ring are also amenable to the present invention. Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include, but are not limited to, lipid moieties such as a cholesterol moiety, cholic acid, a thioether, e.g., hexyl-S-tritylthiol, a thiocholesterol, an aliphatic chain, e.g., dodecandiol or undecyl residues; a phospholipid, a polyamine or a polyethylene glycol chain, or adamantane acetic acid, a palmityl moiety, or an octadecylamine or hexylamino-carbonyl-oxycholesterol moiety. Oligonucleotides, according to the present invention, that are hybridizable to a target nucleic acid preferably comprise from about 5 to about 50 nucleosides. It is more preferred that such compounds comprise from about 8 to about nucleosides, with 15 to 25 nucleosides being particularly preferred. As used herein, a target nucleic acid is any nucleic acid that can hybridize with a complementary nucleic acid-like compound.

Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases, which pair through the formation of hydrogen bonds. "Complementary" and "specifically hybridizable," as used herein, refer to precise pairing or sequence complementarity between first and second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases, which can hydrogen bond with each other. Thus, "specifically hybridizable" and "complementary" are terms which are used to indicate a sufficient degree of complementarity such that stable and specific binding occurs between a compound of the invention and a target RNA molecule.

It is to be understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. Phosphorothioate linkages in the oligonucleotides of the invention are prepared using standard phosphoramidite chemistry on, for example, an automated DNA synthesizer (e.g., Applied Biosystems model 380B) and oxidation with 0.2 M solution of 3H-1,2-benzodithiole-3-one 1,1-dioxide in acetonitrile for the stepwise thiation of the phosphite linkages. Phosphorothioate linkages that have Sp configuration can be prepared generally according to the procedures described in U.S. Pat. Nos. 5,212,295, 5,587,361 and 5,599,797, the contents of which are incorporated by this reference.

In preferred embodiments, 2'-modified amidites are used to synthesize compounds of the invention according to standard phosphoramidite regimes. In especially preferred embodiments, the amidites have a 2'-methoxyethoxy ("MOE") substituent. As will be recognized, this invention concerns oligonucleotides that exhibit increased stability relative to their naturally occurring counterparts. Extracellular and intracellular nucleases generally do not recognize (and, therefore, do not bind to) the compounds of the invention. The modified internucleoside linkages of this invention preferably replace naturally occurring phosphodiester-5'-methylene linkages to confer nuclease resistance.

In another embodiment, a molecule comprising a region specifically binding to the intermediate domain of MyD88 or nucleic acids encoding the intermediate domain of MyD88, (1) suppresses or prevents MyD88 expression but not MyD88$_S$ expression, and (2) activates the c-JUN N-terminal kinase pathway or, alternatively, in another embodiment, the invention provides a molecule which comprises a region specifically binding to nuclear pre-RNA encoding MyD88 or mRNA encoding MyD88$_S$, and (1) suppresses or prevents MyD88$_S$ expression, but not MyD88 expression, and (2) inhibits the down-regulation of TLR-induced nuclear factor kappa B activation and wherein the molecules comprise an antibody or any fragment thereof, a small molecule, a ribozyme, anti-sense nucleic acids or an oligonucleotide, a peptide or a peptidomimetic thereof for use as a medicament.

Thus, in another embodiment, the above-described molecules that can suppress or prevent MyD88$_S$, expression but not MyD88 expression, and inhibit the down-regulation of TLR-induced nuclear factor kappa B activation, can be used for the manufacture of a medicament to treat endotoxin tolerance. Since endotoxin tolerance is a manifestation that occurs during sepsis, the molecules can be used for the manufacture of a medicament to treat sepsis.

The term "medicament to treat" relates to a composition comprising molecules as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The "medicament" may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide, or peptide of the present invention is given at a dose between 1 μg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

In yet another embodiment, the molecules that comprise a region specifically binding to the intermediate domain of MyD88 or nucleic acids encoding the intermediate domain of MyD88, and suppress or prevent MyD88 expression, but not MyD88$_S$ expression, and activate the c-JUN N-terminal kinase pathway can be used for the manufacture of a medicament to activate the c-JUN N-terminal pathway. Since the c-JUN N-terminal kinase stimulation is involved in the induction of apoptosis, the molecules of the present invention can be used for the manufacture of a medicament to treat insufficiency of apoptosis. Insufficiency of apoptosis is a manifestation that frequently occurs in cancer growth and hence, the MyD88$_S$ of the present invention can be used for treatment of cancer.

In another embodiment, a polynucleotide encoding MyD88$_s$ or any homologue or functional fragment thereof, possessing the biological properties of (1) down-regulating the TLR-induced nuclear factor kappa B activation and (2) activating the c-JUN N-terminal kinase pathway can be used as a medicament. Therefore, this aspect of administration for treatment involves the use of gene therapy to deliver the polynucleotide encoding MyD88$_S$ or a functional fragment thereof or a homologue thereof for the treatment of insufficiency of apoptosis.

In yet another embodiment, a polynucleotide encoding MyD88$_S$, or a functional fragment thereof, or a homologue thereof, can be used in a gene therapeutic method for the inhibition of diseases where TLR-induced nuclear factor kappa B activation occurs as, for example, in the case of an infection (for example, an infection from a pathogen such as a virus or bacterium) and, for example, in the case of rheumatoid arthritis, since it has recently been shown in the art that TLR-induced nuclear factor kappa B activation is involved in rheumatoid arthritis. The present invention provides the nucleic acids of MyD88$_S$, or a functional fragment thereof, or a homologue thereof, for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express MyD88$_S$, or a functional fragment thereof, or a homologue thereof, thereby mitigating the effects of absent, partial inactivation, or abnormal expression of MyD88$_S$, or a functional fragment thereof or a homologue thereof. Such gene therapy procedures have been used in the art to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, Nabel & Felgner, *TIBTECH* 11:211–217 (1993); Mintani & Caskey, *TIBTECH* 11:162–166 (1993); Mulligan, *Science* 926–932 (1993); Dillon, *TIBTECH* 11:167–175 (1993); Van Brunt, *Biotechnology* 6(10):1149–1154 (1998); Vigne, *Restorative Neurology and Neuroscience* 8:35–36(1995); Kremer & Perricaudet, *British Medical Bulletin* 51(1); 31–44(1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Methods of non-viral delivery of nucleic acids include lipofection, microinjection, biolistics, virosomes, liposomes, immunoliposomes, polycation or lipid: nucleic acid conjugates, naked DNA, artificial virions, and agent-enhanced uptake of DNA. Lipofection is described in, e.g., U.S. Pat. Nos. 5,049,386, 4,946, 787; and 4,897,355, the contents of which are incorporated by this reference, and lipofection reagents are sold commercially (e.g., Transfectam™ and Lipofectin™). Cationic and neutral lipids that are suitable for efficient receptor-recognition lipofection of polynucleotides include those of Flegner, PCT International Publications WO 91/17424 and WO 91/16024, the contents of which are incorporated by this reference. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); U.S. Pat. Nos. 4,186,183, 4,217, 344, 4,235,871, 4,261,975, 4,485,054, 4,501,728, 4,774,085, 4,837,028, and 4,946,787).

The use of RNA or DNA viral-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral-based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long-term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would, therefore, depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731–2739 (1992); PCT/US94/05700).

In applications where transient expression of the nucleic acid is preferred, adenoviral-based systems are typically used. Adenoviral-based vectors are capable of very high-transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., U.S. Pat. No. 4,797,368; PCT International Publication WO 93/24641, the contents of which are incorporated by this reference; Kotin, *Human Gene Therapy* 5:793–801 (1994); Muzyczka). Construction of recombinant AAV vectors are described in a number of publications, including U.S. Pat. No. 5,173,414; Hermonat & Muzyczka, *Proc. Natl. Acad. Sci. U.S.A.* 81:6466–6470 (1984); and Samulski et al., *J. Virol.* 63:03822–3828 (1989). In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent. pLASN and MFG-S are examples of retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94/22 12133–12138 (1997)). Pa317/pLASN was the first therapeutic vector used in gene therapy trials (Blaese et al., *Science* 270:475–480 (1995)). Transduction efficiencies of 50% greater have been observed for MFG-S-packaged vectors (Ellem et al. *Immunol. Immunother.* 44(1):10–20 (1997); Dranoff et al., *Hum. Gene Ther.* 1:111–2 (1997)).

Recombinant adeno-associated virus vectors (rAAV) are promising alternative gene delivery systems based on the defective and non-pathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998). Replication-deficient recombinant adenoviral vectors (Ad) are predominantly used in transient expression gene therapy, because they can be produced at high titer and they readily infect a number of different cell types. Most adenovirus vectors are engineered such that a transgene replaced the Ad E1a, E1b, and E3 genes; subsequently, the replication-deficient vector is propagated in human 293 cells that supply deleted gene function in trans. Ad vectors can transduce multiple types of tissues in vivo, including non-dividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Sterman et al., *Hum. Gene Ther.* 9:7 1083–1089 (1998); Alvarez et al., *Hum. Gene Ther.* 5:597–613 (1997); Topf et al., *Gene Ther.* 5:507–513 (1998)). Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses' outer surface. The ligand is chosen to have affinity for a receptor known to be present on the cell type of interest. For example, Han et al., *Proc. Natl. Acad. Sci. U.S.A.* 92/9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells. Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via reinfusion of the transfected cells into the host organism) is well known to those of skill in the art. In a preferred embodiment, cells are isolated from the subject organism, transfected with a nucleic acid (gene or cDNA), and reinfused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176: 1693–1702 (1992)). Stem cells are isolated for transduction and differentiation using known methods. For example, stem cells are isolated from bone marrow cells by panning the bone marrow cells with antibodies which bind unwanted cells, such as CD4+ and CD8+ (T-cells), CD45+ (panB cells), GR-1 (granulocytes), and Iad (differentiated antigen-presenting cells) (see Inaba et al., *J. Exp. Med.* 176:1693–1702 (1992)). Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art and, although more than one route can be used to administer a particular composition, a particular route can often provide a more immediate and effective reaction than another route. Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art and, although more than one route can be used to administer a particular composition, a particular route can often provide a more immediate and effective reaction than another route.

It is known from the art that JNK is also required for T-cell differentiation (Dong et al. (2000) *Nature* 405:91; Sabapathy et al. (2001) *J. Exp. Med.* 193:317), and is involved in T helper 1 (Th1) versus Th2 cell polarization during infection (Rincon et al. (2000) *Free Radical Biology and Medicine* 28:1328; Jankovic et al. (2001) *Trends in Immunology* 22:450)). The present invention demonstrates that MyD88$_S$ is constitutively expressed in spleen of Balb/c mice, whereas in the spleen of C57/BL6 mice, MyD88$_S$ is not expressed. The difference in MyD88$_S$ expression corresponds with a true difference in immunological response between both mice strains. It has been well established that in the *Leishmania major* model, mice of the Balb/c strain produce a polarized Th2 response and fail to promote resistance, whereas mice of the C57/BL6 strain, produce a polarized Th1 response and are resistant (Reiner et al. (1995) *Annu. Rev. Immunol.* 13 :151; Guler et al. (1996) *Science* 271: 984)). Since it is known that the Th1/Th2 balance is perturbed during several immunological diseases in a specific embodiment, a polynucleotide encoding MyD88$_S$ or any homologue or functional fragment thereof can be used for the manufacture of a medicament to modulate Th1/Th2 cell polarization.

In yet another embodiment, a polynucleotide encoding MyD88$_S$ or any homologue or functional fragment thereof can be used for the manufacture of a medicament to modulate immunosuppression.

In another embodiment, the invention provides a pharmaceutical composition comprising molecules that (1) comprise a region specifically binding to the intermediate domain of MyD88 or nucleic acids encoding the intermediate domain of MyD88, and wherein the molecules can suppress or prevent MyD88 expression but not MyD88$_S$ expression, and activate the c-JUN N-terminal kinase pathway. In a particular embodiment, the molecules comprise an antibody or any fragment thereof, a small molecule, a ribozyme, oligonucleotides, peptides or peptidomimetics.

In yet another embodiment, the invention provides a pharmaceutical composition comprising molecules that (1) comprise a region specifically binding to nuclear pre-RNA encoding MyD88 or mRNA encoding MyD88$_S$, and wherein the molecules can suppress or prevent MyD88$_S$ expression but not MyD88 expression, and inhibit the down-regulation of TLR-induced nuclear factor kappa B activation. In a particular embodiment, the molecules comprise at least one oligonucleotide.

In yet another embodiment, the invention provides a polypeptide, designated as MyD88$_S$ or any homologue or functional fragment thereof, possessing the biological properties of (1) down-regulating the TLR-induced nuclear factor kappa B activation and (2) activating the c-JUN N-terminal kinase pathway, for use as a medicament.

In another embodiment, the invention provides a method to identify molecules comprising (a) exposing the intermediate domain of MyD88 or nucleic acids encoding the intermediate domain of MyD88 to at least one molecule whose ability to activate the c-JUN N-terminal kinase pathway and down-regulate the TLR-induced nuclear factor kappa B activation is sought to be determined, (b) determining binding or hybridizing of the molecule(s) to the intermediate domain of MyD88 or nucleic acids encoding the intermediate domain, and monitoring the activation of the c-JUN N-terminal kinase pathway and down-regulation of the TLR-induced nuclear factor kappa B activation when administering at least one of the molecule(s).

In yet another embodiment, the invention provides a method to identify molecules comprising (a) exposing the nuclear pre-RNA encoding MyD88 or mRNA encoding MyD88 to at least one molecule whose ability to inhibit the down-regulation of TLR-induced nuclear factor kappa B activation is sought to be determined, (b) determining binding or hybridizing of molecule(s) to the nuclear pre-RNA encoding MyD88 or mRNA encoding MyD88$_S$, and (c) monitoring inhibition of down-regulation of TLR-induced nuclear factor kappa B activation when administering at least one of the molecule(s).

In yet another embodiment, the invention provides a method to identify molecules comprising exposing a region comprising the intermediate domain of MyD88 (SEQ ID NO:14 (amino acid 95 to 172) or nucleic acids encoding SEQ ID NO:14 of MyD88 to at least one molecule whose ability to activate the c-JUN N-terminal kinase pathway and to activate the nuclear factor kappa B activation is sought to be determined, determining binding or hybridizing of the molecule(s) to the intermediate domain of MyD88 or nucleic acids encoding the intermediate domain and monitoring the activation of the c-JUN N-terminal kinase pathway and nuclear factor kappa B activation when administering at least one of the molecule(s).

Thus, the invention provides methods for identifying compounds or molecules (both words can be used interchangeably in this invention) which bind on the ID domain of MyD88 or nucleic acids encoding the ID domain or the nuclear pre-RNA encoding MyD88 or mRNA encoding MyD88. These methods are also referred to as "drug screening assays" or "bioassays" and typically include the step of screening a candidate/test compound or agent for the ability to interact with the ID domain of MyD88 or nucleic acids encoding the ID domain or the nuclear pre-RNA encoding MyD88 or mRNA encoding MyD88. "Compound," in relation to the screening methods described hereinabove, means any inorganic or organic compound, including simple or complex inorganic or organic molecules, oligonucleotides, peptides, peptido-mimetics, proteins, antibodies, carbohydrates, nucleic acids or derivatives thereof. Candidate/test compounds such as small molecules, for example, small organic molecules, and other drug candidates can be obtained, for example, from combinatorial and natural product libraries.

Typically, the assays are cell-free assays which include the steps of combining, for example, the ID domain of MyD88 protein or a nucleic acid encoding the ID domain and a candidate/test compound, for example, under conditions which allow for interaction (e.g. binding) of the candidate/test compound with, for example, the ID domain of MyD88 protein or a nucleic acid encoding the ID domain to form a complex, and detecting the formation of a complex, in which the ability of the candidate compound to interact with, for example, the ID domain of MyD88 protein or a nucleic acid encoding the ID domain is indicated by the presence of the candidate compound in the complex. Formation of complexes between, for example, the ID domain of MyD88 protein or a nucleic acid encoding the ID domain and the candidate compound can be quantitated, for example, using standard immunoassays. For example, the ID domain of MyD88 protein or a nucleic acid encoding the ID domain in such a test may be free in solution, affixed to a solid support, borne on a cell surface, or located intracellularly.

To perform the above-described drug screening assays, it is feasible to immobilize, for example, the ID domain of MyD88 protein or a nucleic acid encoding the ID domain to facilitate separation of complexes from uncomplexed forms of one or both of the proteins, as well as to accommodate automation of the assay. Interaction (e.g., binding) of, for example, the ID domain of MyD88 protein or a nucleic acid encoding the ID domain to a target molecule, can be accomplished in any vessel suitable for containing the reactants. Examples of such vessels include microtiter plates, test tubes, and microcentrifuge tubes. In a particular embodiment, a fusion protein can be provided which adds a domain that allows the protein to be bound to a matrix. For example, the ID domain of MyD88 that is tagged can be adsorbed onto Ni-NTA microtiter plates or a particular heterotetrameric channel-ProtA fusions adsorbed to IgG, which are then combined with the cell lysates (e.g., $^{35}$S-labeled) and the candidate compound, and the mixture incubated under conditions conducive to complex formation (e.g., at physiological conditions for salt and pH). Following incubation, the plates are washed to remove any unbound label, the matrix immobilized and the radiolabel determined either directly or in the supernatant after the complexes are dissociated. Alternatively, the complexes can be dissociated from the matrix, separated by SDS-PAGE, and the level of the ID domain of the MyD88-binding protein found in the bead fraction quantitated from the gel using standard electrophoretic techniques. Other techniques for immobilizing protein on matrices can also be used in the drug screening assays of the invention. For example, the ID domain of MyD88 can be immobilized utilizing conjugation of biotin and streptavidin.

Biotinylated-particular ID domain of MyD88 can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemical). Alternatively, antibodies reactive with the ID domain of MyD88 can be derivatized to the wells of the plate and the ID domain of MyD88 can be trapped in the wells by antibody conjugation.

As described above, preparations of the ID domain of MyD88 and a candidate compound are incubated in particular MyD88 ID domain-presenting wells of the plate, and the amount of complex trapped in the well can be quantitated. Methods for detecting such complexes, in addition to those described above for the GST-immobilized complexes, include immunodetection of complexes using antibodies reactive with the ID domain of MyD88-target molecule or which are reactive with the ID domain of MyD88 and compete with the target molecule, as well as enzyme-linked assays which rely on detecting an enzymatic activity associated with the target molecule.

Another technique for drug screening which provides for high throughput screening of compounds having suitable binding affinity to the ID domain of MyD88$_S$ is described in detail in "Determination of Amino Acid Sequence Antigenicity" by Geysen HN, WO 84/03564, published on Sep. 13, 1984. In summary, large numbers of different small peptide test compounds are synthesized on a solid substrate, such as plastic pins or some other surface. The protein test compounds are reacted with the ID domain of MyD88 and washed. Bound ID domain of MyD88 is then detected by methods well known in the art. A purified ID domain of MyD88 can also be coated directly onto plates for use in the aforementioned drug screening techniques. Alternatively, non-neutralizing antibodies can be used to capture the peptide and immobilize it on a solid support. This invention also contemplates the use of competitive drug screening assays in which neutralizing antibodies capable of binding the ID domain of MyD88 specifically compete with a test compound for binding the ID domain of MyD88.

EXAMPLES

Identification of an Inducible Splice Variant of MyD88

The mouse MyD88 gene is organized in five exons and four introns. The first exon (corresponding to amino acids 1–109) encodes the DD, the second exon (corresponding to amino acids 110–154) the ID, and the three last exons (corresponding to amino acids 155–296) the TIR domain (see FIG. 1a). RT-PCR for MyD88 on RNA isolated from the murine macrophage cell line Mf4/4 revealed two cDNA species of 890 and 747 bp, respectively (FIG. 1b). The sequence of the more abundant, larger isoform (also termed MyD88$_L$) was found to be identical to the published sequence of full length MyD88 (6, 7). Sequence analysis of the smaller isoform showed that it corresponds to a splice variant of MyD88, lacking exon 2, and subsequently referred to as MyD88$_S$. Excision of exon 2 in MyD88$_S$ leads to an in-frame deletion of the complete ID (aa 110–154), resulting in a protein isoform of approximately 27 kDa (FIG. 1a). The expression pattern of MyD88$_S$ mRNA was analyzed by PCR on a Balb/c mouse multiple tissue cDNA panel (FIG. 1c). MyD88$_L$ mRNA was present in all adult mouse tissues examined, though at different expression levels. In contrast, MyD88$_S$ could be detected only in the spleen and weakly in the brain, suggesting that its expression is tightly regulated. Interestingly, MyD88 mRNA was the major species in splenic extracts from C57/BL6 mice. However, MyD88$_S$ mRNA levels in the spleen of these mice were strongly up-regulated 1 hour after injection of mice with TNF. Sequencing of this up-regulated mRNA species, as well as PCR amplification of a MyD88$_S$ specific band of 438 bp with a primer that was designed across the exon 1-exon 3 boundary, confirmed its identity as MyD88$_S$. MyD88$_S$ expression in spleen of TNF-treated mice was also studied at the protein level. For these purposes, C57/BL6 mice were injected with 20 µg TNF and spleen homogenates were prepared 1 hour, 4 hours, or 13 hours after TNF injection, respectively. Immunoblotting of these extracts with MyD88-specific antibodies showed that MyD88 was constitutively expressed in untreated and TNF-treated mice. In contrast, MyD88$_S$ expression was not detectable in untreated mice or mice treated for 1 hour with TNF. However, after 4 hours and 13 hours TNF treatment, specific induction of a 27 kDa band corresponding to MyD88$_S$ was observed. In conclusion, these results clearly demonstrate the mouse strain-specific and inducible expression of MyD88$_S$ in the spleen. Apart from the constitutive expression of MyD88$_S$ in the spleen and brain of Balb/c mice and the inducible expression of MyD88$_S$ in C57/BL6 mice, we also found constitutive expression of MyD88$_S$ in the testis and eye of C57/BL6 mice. Based on the homology between mouse and human MyD88$_S$, we cloned the human equivalent of MyD88$_S$ (depicted in SEQ ID NO:1 for the nucleotide sequence and SEQ ID NO:2 for the amino acid sequence). The murine MyD88$_S$ is depicted in SEQ ID NO:3 for the nucleotide sequence and SEQ ID NO:4 for the amino acid sequence.

MyD88$_S$ does not Activate NF-κB but Behaves as a Dominant Negative Inhibitor

Figure 2:
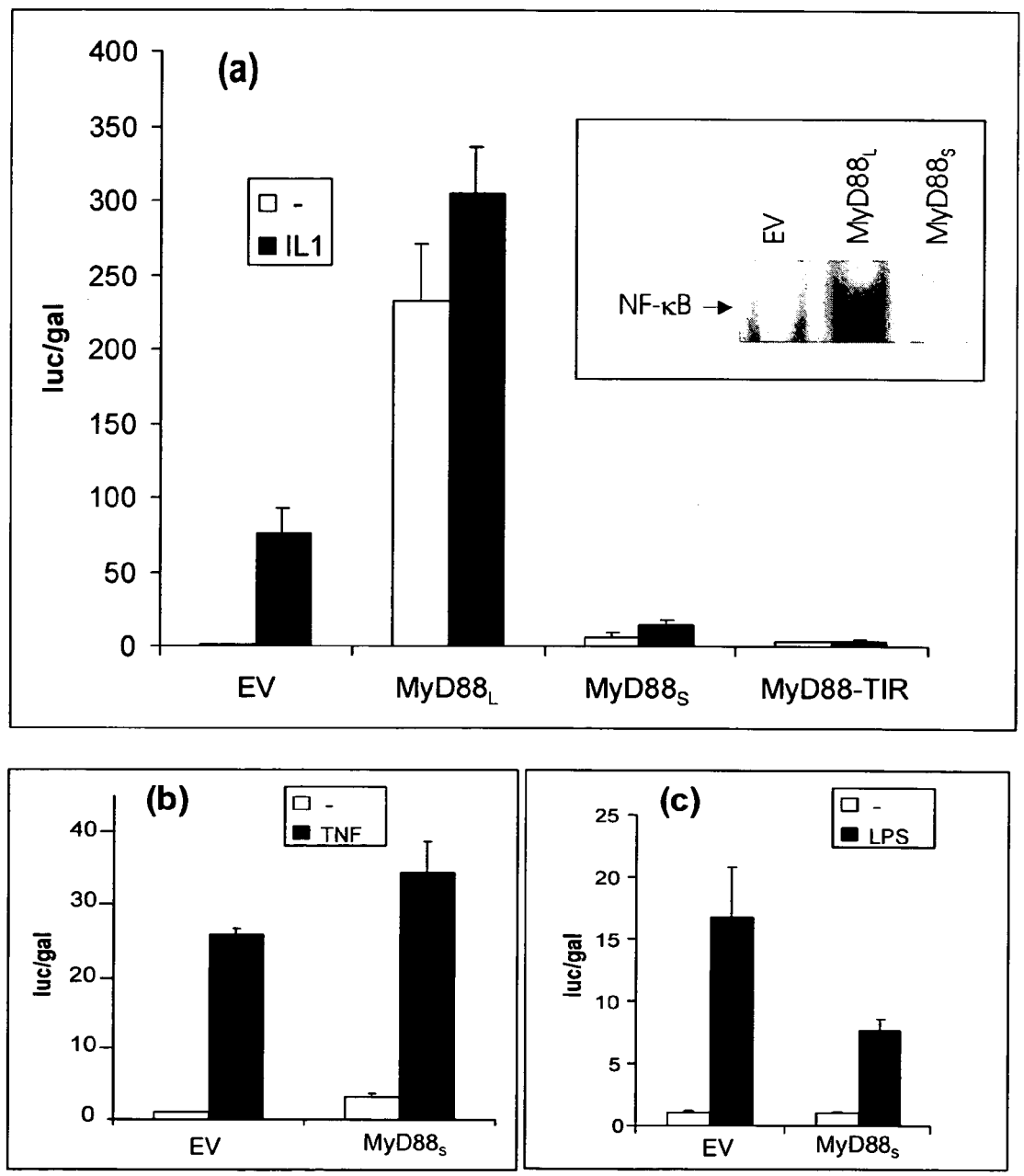
FIG. 2: MyD88$_S$ specifically inhibits IL-1- and LPS-induced NF-κB activation. HEK293T cells (a)–(b) or Mf4/4 cells (c) were transiently transfected with the NF-κB-dependent luciferase reporter plasmid pNFconluc and the β-galactosidase reporter plasmid pPGKneogal, each time combined with an expression plasmid for either MyD88$_S$, MyD88$_L$, MyD88-TIR or empty vector (EV) as indicated. Forty-eight hours post-transfection, cells were either left untreated or stimulated for 6 hours with 100 ng/ml IL-1β (a), 100 ng/ml TNF (b) or 100 ng/ml LPS (c). Luciferase activity in cell extracts is normalized for differences in transfection efficiency on the basis of β-galactosidase activity. Values are the mean (±standard error) of three different transfections within a single experiment, and are expressed as fold induction relative to the unstimulated EV control. (a Insert) Electrophoretic mobility shift assay with nuclear extracts prepared from HEK293T cells that were transiently transfected with empty vector (EV), MyD88$_L$ or MyD88$_S$. The shift in migration of a $^{32}$P-labeled Ig κB DNA-oligo upon binding of NF-κB is shown. Proper expression of MyD88$_S$ and MyD88$_L$ was verified by western blot analysis (data not shown).

Previous reports clearly showed that ectopic expression of MyD88 strongly activates NF-κB (1–3). To test whether MyD88$_S$ activates NF-κB, HEK293T cells were transiently transfected and analyzed for NF-κB activation by reporter gene (FIG. 2a) or gel shift assay (FIG. 2a insert). In contrast to MyD88$_L$, MyD88$_S$ overexpression did not induce DNA binding of NF-κB or NF-κB reporter gene activation. These results point to an important role for the ID of MyD88 in NF-κB activation and are in agreement with previous findings of Medzhitov et al. (2), who demonstrated that the DD alone is insufficient for NF-κB activation. Co-expression of MyD88$_L$ with increasing amounts of MyD88$_S$ showed that already low expression levels of MyD88$_S$ significantly reduced the ability of MyD88$_L$ to activate NF-κB. In line with these results, MyD88$_S$ overexpression almost completely inhibited IL-1-induced NF-κB activation (FIG. 2a), which is similar to the previously described effect of over-expression of the TIR domain of MyD88 (1). As expected, we did not observe any inhibitory effect of MyD88$_S$ on TNF-induced NF-κB activation (FIG. 2b). Because HEK 293T cells are unresponsive to LPS, we tested the effect of MyD88$_S$ on LPS-induced NF-iB activation in Mf4/4 macrophages. Only a partial inhibitory effect of MyD88$_S$ could be observed (FIG. 2c), probably due to the presence of MyD88-independent signaling pathways emerging from the TLR4 receptor (14). In conclusion, these results demonstrate that MyD88$_S$ can function as a negative regulator of IL-1- and LPS-induced NF-κB activation.

MyD88$_S$ Competes with MyD88$_L$ for Binding to the IL-1R/IL-1RacP Complex

Figure 3:
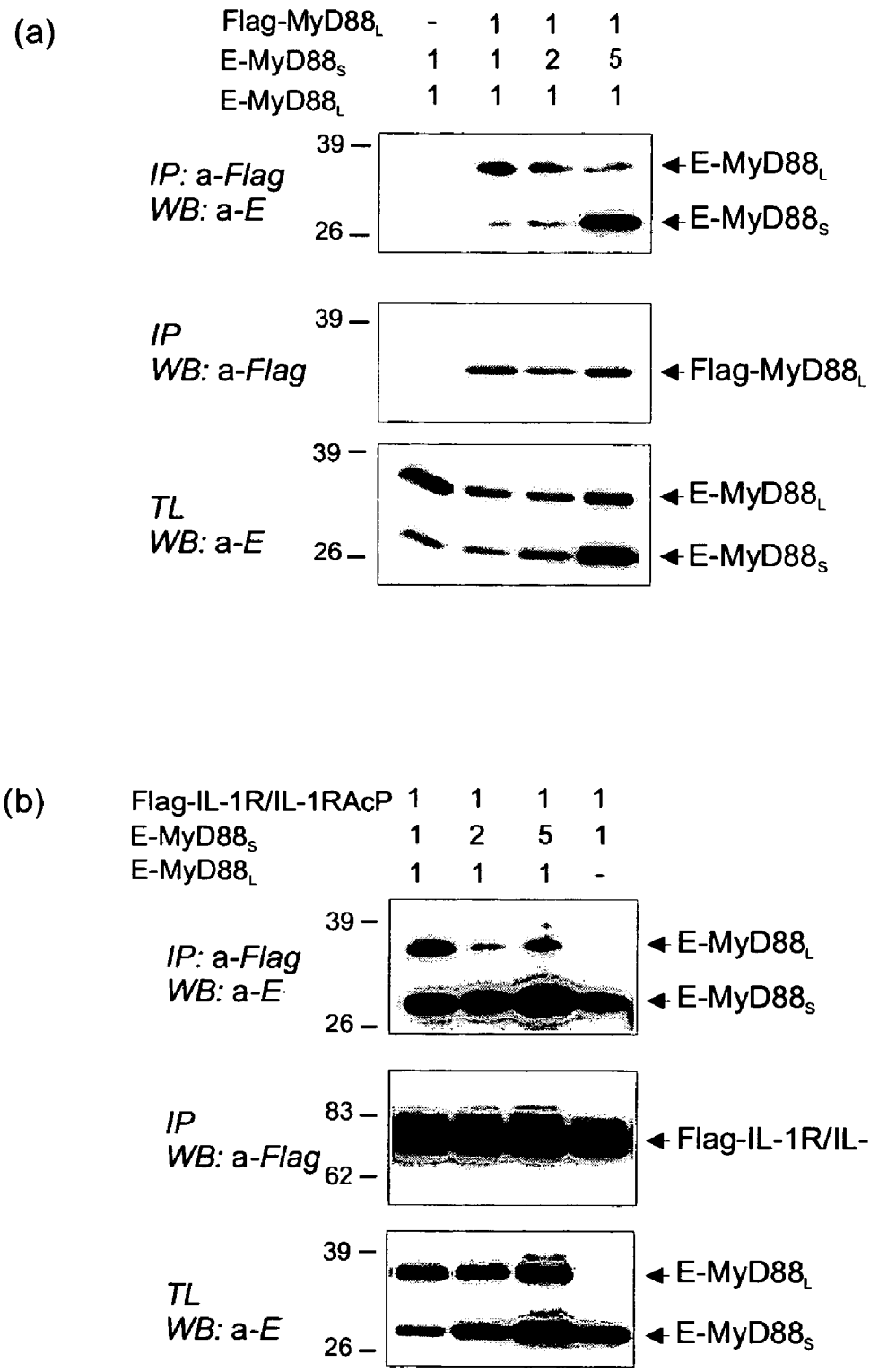
FIG. 3: MyD88$_S$ competes with MyD88$_L$ for dimer formation (a) and recruitment to the IL-1R (b). HEK293T cells were transiently transfected with different expression plasmids for epitope-tagged proteins (amounts shown in µg on top of each figure). Cell extracts were immunoprecipitated (IP) with anti-Flag antibody, and co-immunoprecipitating proteins were revealed by western blotting (WB) with anti-E-tag antibody (upper panel). Immunoprecipitation of Flag-tagged proteins was confirmed by western blotting (middle panel). Expression of transfected proteins was confirmed by western blotting of total lysates (TL) with anti-E-tag antibody (lower panel).

To find a mechanistic explanation for the dominant negative effect of MyD88$_S$ in the IL-1-induced signaling pathway to NF-κB, we investigated by co-immunoprecipitation whether the splice variant is still present in the IL-1R/IL-1RAcP complex. MyD88 has previously been shown to be recruited as a homodimer to the activated IL-1 R(3). Both the DD and the TIR domain are required for homodimerization (3). Therefore, we first tested if MyD88$_S$ was still able to form dimers with MyD88 upon expression in HEK293T cells. The results shown in FIG. 3a demonstrate that E-MyD88$_S$ as well as E-MyD88$_L$ are co-immunoprecipitated specifically with Flag-MyD88$_L$. Furthermore, increasing the concentration of E-MyD88$_S$ favors the formation of MyD88$_S$-MyD88$_L$ heterodimers. Next, we investigated the binding of MyD88$_S$ to the IL-1R/IL-1RAcP complex. Co-immunoprecipitation revealed that MyD88$_S$ still binds to the IL-1R/IL-1RAcP complex (FIG. 3b). This is in agreement with previous reports showing that the TIR domain of MyD88—which is intact in MyD88$_S$—is necessary and sufficient for IL-1R binding (1). When MyD88$_S$ and MyD88 were co-expressed, low amounts of MyD88$_S$ already competed with MyD88 for binding to the IL-1R/IL-1RAcP complex (FIG. 3b). In summary, these results demonstrate that upon expression of MyD88$_S$, MyD88-MyD88$_S$ heterodimers are formed and recruited to the IL-1 Rcomplex, suggesting that the dominant negative effect induced by MyD88$_S$ is related to its inability to bind or to activate downstream signaling molecules, an obvious candidate being IRAK.

Figure 4:
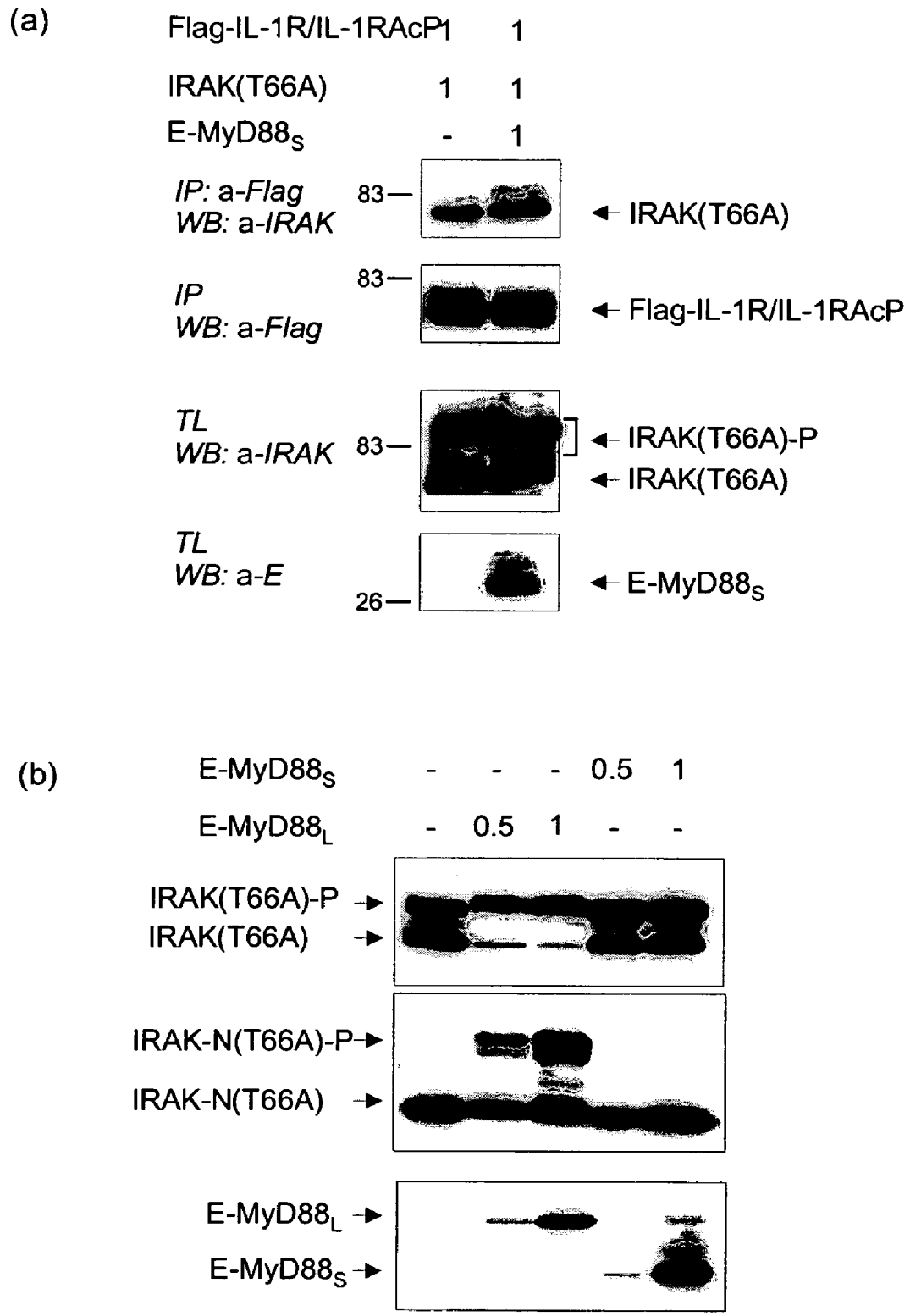
FIG. 4: MyD88$_S$ still allows IRAK recruitment to the IL-1R complex (a), but no longer induces IRAK phosphorylation (b). (a) HEK293T cells were transiently transfected with expression plasmids for epitope-tagged proteins (amounts shown in µg on top of each figure). Cell extracts were immunoprecipitated (IP) with anti-Flag antibody and co-immunoprecipitating proteins were revealed by western blotting (WB) with an anti-IRAK antibody (upper panel). Immunoprecipitation of Flag-tagged proteins was confirmed by western blotting (second panel). Expression of transfected proteins was confirmed by western blotting of total lysates (TL) with the indicated antibodies (two lower panels). Upper bands of IRAK represent phosphorylated proteins (IRAK-P), lower bands represent unphosphorylated IRAK. (b) HEK293T cells were transiently transfected with expression plasmids for epitope-tagged MyD88 (amounts shown in µg on top of the figure), in combination with either an expression plasmid for IRAK(T66A) or IRAK-N(T66A). Cell lysates were analyzed by western blotting and probed with anti-IRAK (upper and middle panel) or anti-E-tag antibody (lower panel).

MyD88$_S$ Still Allows the Recruitment of IRAK to the IL-1R, but does not Induce IRAK Phosphorylation MyD88 binds IRAK primarily through DD—DD interactions, therefore, it was unlikely that removal of the ID would interfere with IRAK binding. Indeed, MyD88$_S$ still binds IRAK (data not shown) and has no effect on its recruitment into the IL-1R complex (FIG. 4a). Previously, we have shown that MyD88 triggers IRAK phosphorylation (4). This can simply be demonstrated by co-expression of MyD88 and a mutant version of IRAK, IRAK(T66A) which, in contrast to wild-type IRAK, is not rapidly degraded by co-expression with MyD88. IRAK(T66A) migrates as a series of phosphospecies, which are converted to a hyper-phosphorylation state (corresponding to the slower migrating species) by co-expressing MyD88 (FIG. 4b upper panel and (4)). We, therefore, wished to test whether MyD88$_S$ could similarly induce phosphorylation of IRAK(T66A) and found that MyD88$_S$ did not induce IRAK phosphorylation. Similar results were obtained when we used an N-terminal deletion construct of IRAK(T66A) (IRAK-N(T66A), residues 1–208 (Burns K. et al. (2000) *Nat. Cell. Biol.* 2:346)), that, in contrast to full length IRAK, migrates as a single species in unstimulated conditions (FIG. 4b, middle panel). Many studies provided evidence that IRAK undergoes hyperphosphorylation, and presumably ubiquitination, upon receptor recruitment (10, 11, 3). Phosphorylation of IRAK has previously been shown to be essential for interaction of IRAK with TRAF6 (12). Li et al. (2001) *PNAS* 98 :4461, demonstrated that deletion mutants of IRAK that are not modified upon IL-1 stimulation are unable to activate NF-κB. The inability of MyD88$_S$ to activate NF-κB as well as to induce IRAK phosphorylation further suggests that both events are correlated. Although MyD88 is known to be important for IRAK phosphorylation (4), the exact mechanism of IRAK phosphorylation is still unknown. Reconstitution experiments of IRAK-deficient cells with kinase-inactive IRAK have shown that kinase-inactive IRAK still becomes phosphorylated in response to IL-1 (11), demonstrating that IRAK phosphorylation must be due to another kinase.

MyD88 is Required for IRAK-4-Induced IRAK-1 Phosphorylation

For some time it was speculated that IRAK-1 was phosphorylated via its own kinase activity. However, this idea was challenged by the discovery that a kinase dead mutant of IRAK-1 (subsequently referred to as IRAK-1KD) was phosphorylated in an IRAK-1-deficient cell line. A second kinase was postulated to phosphorylate IRAK-1 and perhaps to activate IRAK-1's own kinase activity. Recently IRAK-4, so called for its homology to other members of the IRAK-1 family (other members include the kinase inactive IRAK-2 and IRAK-M/3), was identified as a candidate for the IRAK-1 kinase (Wesche H. et al (1999) *J. Biol. Chem.* 274: 19403). This was based on in vitro kinase assays and the observation that IL-1-induced degradation of IRAK-1 was partially blocked by overexpression of a kinase-inactive mutant of IRAK-4. To obtain additional evidence that IRAK-4 is a kinase for IRAK-1, we developed a co-expression assay in HEK293T cells. IRAK-4 was co-transfected together with IRAK-1KD (IRAK-1D340N) (used because it cannot self-phosphorylate like overexpressed wild-type IRAK-1) and phosphorylation monitored by the appearance of a slower migrating species in SDS-PAGE. As predicted, IRAK-4 induced phosphorylation of IRAK-1KD. That phosphorylation was specifically induced by IRAK-4 was confirmed by the observation that co-expression of IRAK-1KD with two different IRAK-4 kinase dead mutants, IRAK-4KD (IRAK-4KK213AA or IRAK-4D311N), did not similarly induce IRAK-1KD phosphorylation. Although co-expression of IRAK-4 clearly induced IRAK-1 phosphorylation, only a partial conversion to the phosphorylated species was observed. Addition of MyD88, however, significantly enhanced IRAK-4-induced IRAK-1KD phosphorylation, suggesting that MyD88 stimulates IRAK-4's activity. This was confirmed by an in vitro kinase assay carried out on immunoprecipitated IRAK-1KD showing significant phosphorylation of IRAK-1KD, when immunoprecipitated from cell extracts co-expressing MyD88 and IRAK-4, but not IRAK-4KD. As MyD88 binds to IRAK-1KD (MyD88 does not bind the hyperphosphorylated form of IRAK-1 induced by its overexpression and was recently reported to bind IRAK-4), the simplest explanation for the observed finding was that MyD88 modulates contact of IRAK-1 and IRAK-4. To test this, IRAK-1KD and IRAK-4 interactions were analyzed in the presence or absence of MyD88 and/or $MyD88_S$. As previously reported, IRAK-4 and IRAK-1KD do not directly associate. However, addition of MyD88 but not $MyD88_S$ permitted assembly of a complex containing both IRAKs. MyD88 thereby appears to act like a hinge inducing the proximity of IRAK-1 and IRAK-4. Interestingly, phosphorylated IRAK-1 is stably detected together with MyD88, IRAK-1 and IRAK-4, suggesting that MyD88/IRAK-1 interactions are destabilized only after multiple sites are phosphorylated on IRAK-1.

$MyD88_S$ Blocks IRAK-4-Induced IRAK-1 Phosphorylation

Unlike MyD88, $MyD88_S$ does not stimulate IRAK-4-induced IRAK-1KD phosphorylation. In fact, in vitro phosphorylation of IRAK-1KD induced by IRAK-4 co-expression was completely inhibited when $MyD88_S$ was co-expressed. Further, $MyD88_S$ inhibited MyD88's stimulatory effect on IRAK-4-induced IRAK-1KD phosphorylation in a dose-dependent manner.

$MyD88_S$ does not Bind to IRAK-4 and Blocks Recruitment of IRAK-4 to the IL-1Rs To characterize the underlying mechanism by which $MyD88_S$ blocks IRAK-1 phosphorylation, we initially analyzed if MyD88 and IRAK-4 associate. We did not expect the contrary, considering that MyD88 binds IRAK primarily through DD-DD interactions. However, $MyD88_S$/IRAK-4 complexes were not detected, despite the strong association of $MyD88_S$ and IRAK-1KD under similar conditions of co-immunoprecipitation. This, therefore, suggested that the ID of MyD88 is required for this association with IRAK-4. To confirm this, the precise region of MyD88 mediating its interaction with IRAK-4 was mapped by yeast 2-hybrid and co-immunoprecipitation binding assays. These assays confirm that MyD88 does, and $MyD88_S$ does not, interact with IRAK4. However, the ID in itself is insufficient, suggesting that MyD88 interacts with IRAK-4 via a peptide spanning both the ID and adjacent amino acids in the DD (we cannot exclude that the first 17 amino acids of the TIR are important for binding) or that the ID induces a conformation of MyD88, exposing residues in the DD that are critical for interactions between the two proteins.

The above examples show that $MyD88_S$ acts as a negative regulator by its incapacity to bind to IRAK-4 and thus to prevent IRAK-4-induced IRAK-1 phosphorylation. Under chronic conditions of inflammation or following prolonged exposure to LPS, $MyD88_S$ is expressed. As a result, the above sequence of events is halted. IRAK-4 is not recruited to the IL-1Rs/TLRs, therefore, IRAK-1 is not phosphorylated/activated and, as a consequence, signal transmission is interrupted. In conclusion, $MyD88_S$ acts as a negative regulator of IL-1β/LPS-induced NF-κB activation by preventing IRAK-4's access to its substrate.

$MyD88_S$ is Involved in Endotoxin Tolerance

Figure 5:
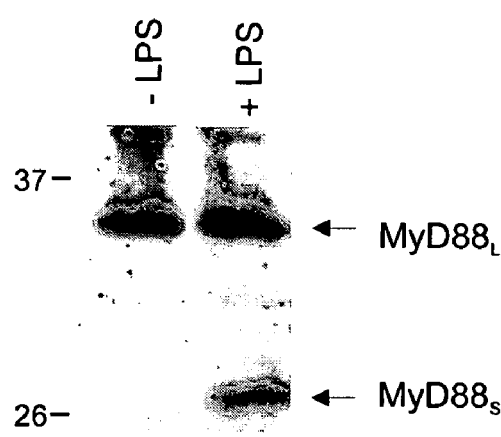
FIG. 5: Expression of endogenous MyD88$_S$ in LPS-pretreated human monocytes is associated with a diminished LPS-response. THP-1 cells were either left untreated or treated with 500 ng/ml LPS for 16 hours, washed three times with serum-free RPMI, resuspended in fresh culture medium and restimulated with 500 ng/ml LPS for different time periods. (a)–(b) MyD88$_S$ and IκB-α expression levels were analyzed by western blotting after 2 hours and 20 minutes restimulation with LPS, respectively. (c) TNF levels in the supernatant were measured in a TNF-bioassay after 3 hours restimulation with LPS and are expressed as the mean ± standard error of three different samples. No signal means that TNF levels were below the detection limit of the assay (=25 pg/ml).
Figure 5:
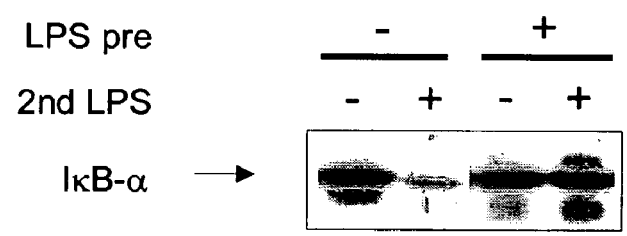
Figure 5:
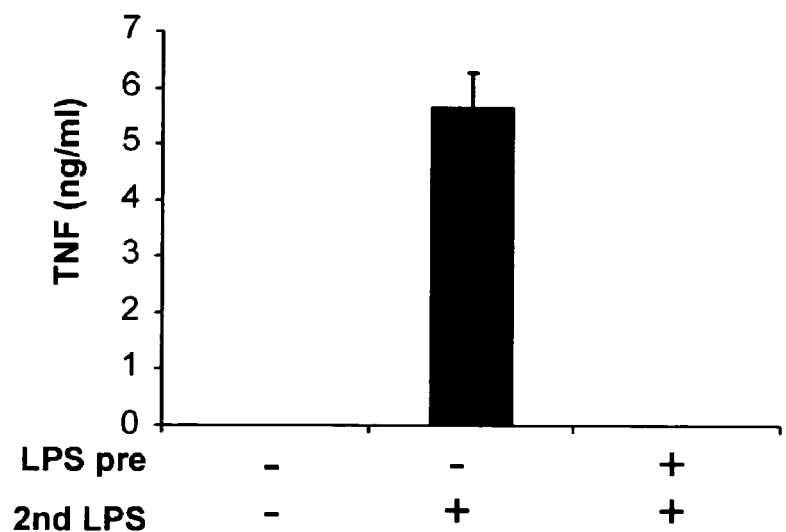

If $MyD88_S$ indeed functions as a negative regulator of IL-1 and LPS-signaling pathways, we rationalized that the expression of endogenous $MyD88_S$ must be tightly controlled. Analysis of $MyD88_S$ protein expression in cell lines of different origin did not reveal any detectable expression level. However, prolonged incubation (16 hours) of the human THP-1 monocytic cell line with LPS resulted in $MyD88_S$ expression (FIG. 5a). We then tested if the induction of endogenous $MyD88_S$ correlated with a defect in LPS-signaling to NF-κB. Indeed, LPS-induced IκB degradation and TNF secretion is inhibited in LPS-pretreated monocytes (FIGS. 5b and 5c). It has been well established that prolonged incubation with LPS induces endotoxin tolerance in monocytes which makes them refractory to subsequent LPS challenges. Although one cannot exclude additional mechanisms in the development of endotoxin tolerance, it is worth mentioning that recently, a defect in the phosphorylation and activation of IRAK has been described in endotoxin-tolerant cells. Taking into consideration that $MyD88_S$ expression prevents the phosphorylation of IRAK, it is possible that LPS-inducible expression of $MyD88_S$ contributes to endotoxin tolerance.

In conclusion, the tissue-specific and inducible expression of a splice variant of MyD88 that acts as a dominant-negative inhibitor of IL-1 and LPS-induced NF-κB activation implicates an important role for alternative splicing of MyD88 in the regulation of the cellular response to IL-1, LPS and possibly other triggers of the IL-1R/TLR superfamily. Furthermore, our results also demonstrate that MyD88 not only functions as a passive adaptor protein, but also plays an active role in the phosphorylation and activation of IRAK through its ID.

Analysis of $MyD88_S$ in Sepsis Patients $MyD88_S$ expression is analyzed in freshly isolated peripheral blood mononuclear cells (PBMC) that are isolated from sepsis patients. Blood samples are taken on day one (=day of arrival at intensive care unit) and day 7. Serum is prepared from a fraction of the blood sample and used in bioassays for the determination of the presence of cytokines (TNF, IL-1). Another fraction is used for the preparation of PBMC, in which the expression of $MyD88_S$ is analyzed by western blotting.

Figure 6:
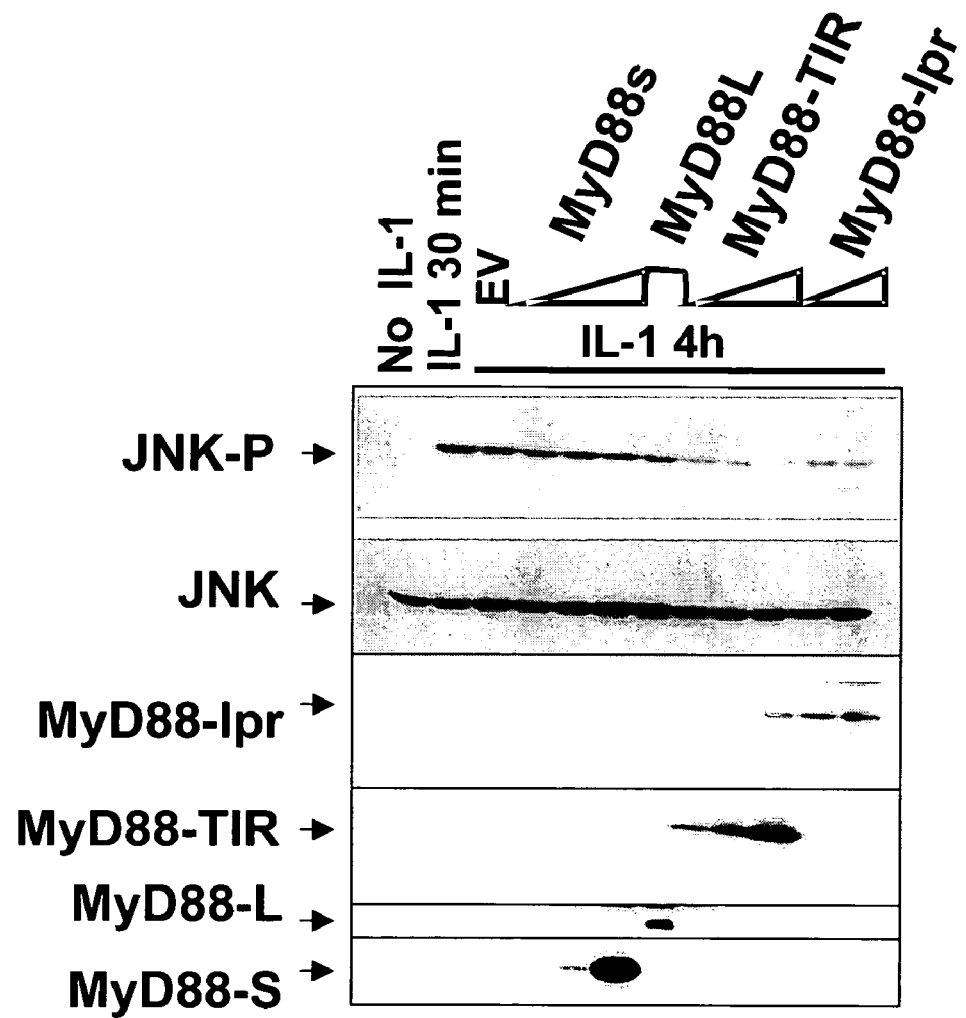
FIG. 6: MyD88$_S$ does not inhibit IL-1-induced activation of JNK. HEK293T cells were transiently transfected with an expression plasmid for Flag-tagged JNK, together with increasing concentrations of different MyD88 proteins. Two days later, cells were treated for 30 minutes or 4 hours with IL-1 and analyzed for JNK phosphorylation by immunoblotting with a phospho-JNK specific antibody (upper panel). Total expression of JNK was verified by western blotting with anti-Flag This shows that IL-1 induces the phosphorylation of JNK after 30 minutes as well as after 4 hours treatment. Co-expression of MyD88-TIR (deletion mutant of MyD88 which only expresses the TIR domain) or MyD88-1pr (point mutant in the death domain which disrupts the structure of the death domain), almost completely prevented the IL-1 induced JNK phosphorylation, confirming the previously shown dominant-negative effect of these mutants. In contrast to MyD88-TIR and MyD88-1pr, co-expression of MyD88$_S$ did not prevent IL-1-induced phosphorylation of JNK, although MyD88$_S$ inhibits IL-1 induced NF-κB activation under similar conditions. Expression of all proteins was verified by Western blot analysis (other panels).

MyD88$_S$, which Inhibits IL-1-Induced NF-κB Activation, does not Inhibit IL-1 Induced Activation of JNK HEK 293T cells which stably express the IL-1R, were transiently transfected with an expression plasmid for Flag-tagged JNK and increasing concentrations of different MyD88 proteins. Cells were treated for 30 minutes or 4 hours with IL-1 and analyzed for JNK phosphorylation by immunoblotting with a phospho-JNK specific antibody (upper panel of FIG. 6). Total expression of JNK was verified by western blotting with anti-Flag. This shows that IL-1 induces the phosphorylation of JNK after 30 minutes as well as after 4 hours treatment. Co-expression of MyD88-TIR (deletion mutant of MyD88 which only expresses the TIR domain) or MyD88-1pr (point mutant in the death domain which disrupts the structure of the death domain), almost completely prevented the IL-1-induced JNK phosphorylation, confirming the previously shown dominant-negative effect of these mutants. In contrast to MyD88-TIR and MyD88-1pr, co-expression of MyD88$_S$ did not prevent IL-1-induced phosphorylation of JNK, although MyD88$_S$ inhibits IL-1-induced NF-κB activation under similar conditions. Expression of all proteins was verified by western blot analysis. These results demonstrate that MyD88$_S$ expression can specifically prevent IL-1-induced NF-κB activation, without changing JNK activation.

Figure 7:
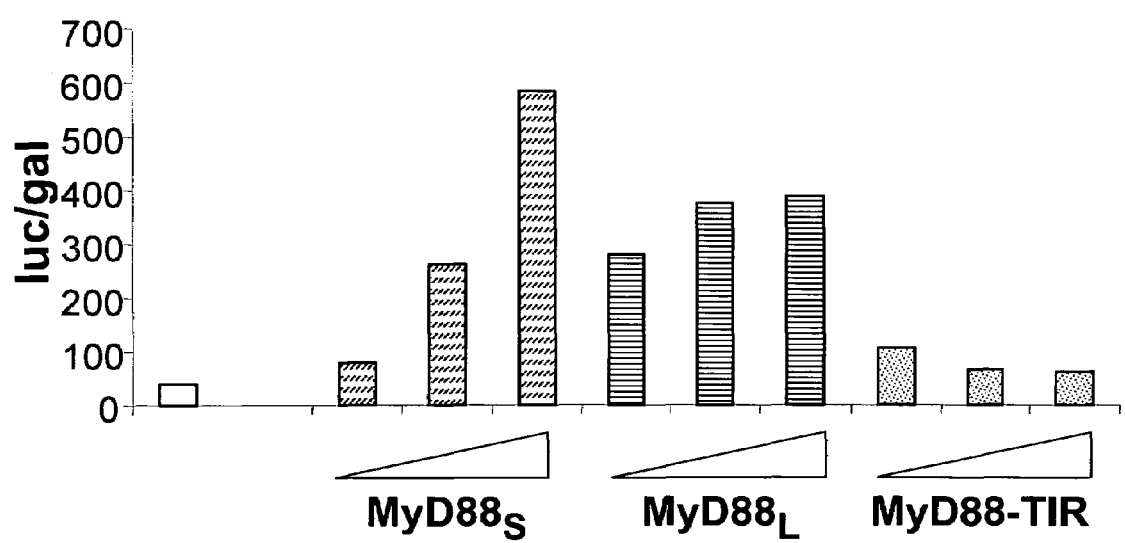
FIG. 7: MyD88$_S$ induces AP-1-dependent gene expression. HEK293T cells were transiently transfected with an AP-1-dependent luciferase reporter construct, together with increasing amounts of MyD88$_S$, MyD88$_L$ or MyD88 TIR expression plasmids. Two days after transfection, cell extracts were prepared and luciferase activity determined. Differences in transfection efficiency were normalized by co-transfecting a constitutively expressed βgal expression plasmid and values are expressed as luc/gal.

MyD88$_S$, which is Ineffective to Activate NF-κB-Dependent Gene Expression, Still Activates JNK and Induces AP-1 (c-fos/c-jun)-Dependent Gene Expression MyD88$_S$ is no longer able to activate NF-κB-dependent gene expression. In order to analyze whether MyD88$_S$ is still able to activate AP-1-dependent gene expression, we transiently transfected HEK293 cells with an AP-1-dependent luciferase reporter construct, together with increasing amounts of MyD88$_S$, MyD88$_L$ or MyD88 TIR-expression plasmids. Cell extracts were prepared and luciferase activity determined. Differences in transfection efficiency were normalized by co-transfecting a constitutively expressed βgal expression plasmid and values are expressed as luc/gal. As shown in FIG. 7, both MyD88$_S$ and MyD88$_L$ still activate an AP-1-dependent reporter construct. Since AP-1 is regulated by JNK, we investigated if MyD88$_S$ was still able to activate JNK phosphorylation. We co-transfected a Flag-tagged expression vector for JNK1 with expression plasmids for MyD88 or MyD88$_S$, and analyzed JNK phosphorylation by immunoblotting with phospho-JNK specific antibodies. Both in the presence of MyD88 as well as in the presence of MyD88$_S$, a marked induction of phosphorylated JNK could be observed. These data show that the NF-κB and JNK/AP-1 pathways diverge at the level of MyD88. MyD88$_S$ allows specific activation of the JNK pathway and AP-1-dependent gene expression, while blocking NF-κB-dependent gene expression. Obtaining specificity might be important in view of specifically modulating gene expression linked with inflammation/immunity and T-cell differentiation, but also to modulate the role of JNK in cell survival (e.g., IL-1-induced apoptosis of islet cells; TNF-induced apoptosis of cancer cells; neuronal apoptosis), without modulating the anti-apoptotic NF-κB pathway.

Specific Down-Regulation of MyD88 Via RNA-Inhibition

It is possible to selectively knock-down MyD88$_L$ through the use of RNA inhibition (RNAi) with a siRNA duplex that is specifically directed to the sequence that encodes the intermediate domain of MyD88 that is missing in MyD88$_S$. The siRNAs duplexes are transfected in the cells of interest by oligofectamin (Life Technologies) and the transfection efficiency reaches 90–95%. Efficient knock-down of the gene of interest is verified by western blot analysis or RT-PCR.

The following sequences (corresponding to part of the intermediate domain) are used to specifically knock down MyD88$_L$:

```
murine MyD88:
5'-AACCAGGAGTCCGAGAAGCCTTT-3'    (SEQ ID NO:5)

human MyD88:
5'-AAGCCTTTTACAGGTGGCCGCTGT-3'   (SEQ ID NO:6)
```

MyD88$_S$, which lacks the ID, will not be affected by these siRNA duplexes. This allows us to study the effect of MyD88$_S$ expression in a MyD88$_L$ negative background. Such cells should only respond to LPS or IL-1 by JNK and AP-1 activation, whereas NF-κB activation is blunted. Moreover, JNK activation will be sustained because of the inhibiting effect of NF-κB on the JNK pathway is no longer occurring.

Specific Down-Regulation of MyD88$_S$ Via RNA-Inhibition

It is possible to selectively knock-down MyD88$_S$ through the use of RNAi with a siRNA duplex that is specifically directed to the sequence that forms the boundary between the death domain and TIR domain of MyD88$_S$.

The following sequences (corresponding to the boundary of the DD and TIR domain (exon 1-exon 3 boundary) are used to specifically knock down MyD88$_S$:

```
murine MyD88:
5'-aagtcgcgcatcggacaaacg-3'      (SEQ ID NO:7)

human MyD88:
5'-CATTGGGCATATGCCTGAGCG-3'      (SEQ ID NO:8)
```

MyD88$_L$, which lacks this exon 1-exon 3 boundary, will not be affected by these siRNA duplexes. This allows us to study the response of cells in the absence of MyD88$_S$ expression, and will prevent the negative regulation of NF-κB activation in tolerant cells.

Interference with Alternative Splicing of MyD88

We demonstrated that in THP-1, which were treated for 16 hours with LPS, MyD88$_S$ expression is induced by alternative splicing of MyD88. Alternative splicing of MyD88 to MyD88$_S$ can be prevented by the use of antisense oligos, which target a particular 3' intron-exon junction and make it less likely that this site shall be recognized as the acceptor site in the splicing process (Lim and Hertel (2001) *J. Biol. Chem.* 276: 14476). MyD88$_S$ is formed by exon skipping of exon 2. This means that the 3' acceptor splice sites of exon 2 and exon 3 compete with each other for the 5' donor site from exon 1. The underlying molecular mechanism is unknown, but might involve the LPS-induced disruption of a putative exon splicing enhancer in exon 2, an element which promotes splice site and exon recognition by assisting in the recruitment of the splicing machinery (e.g., SR proteins, hnRNP proteins; Chabot (1996) *Trends in Genetics* 12:472). By administration of antisense oligos designed against the intron-exon junction of the 3' acceptor splice site of exon 3, the balance may be tilted to favor exon 2 inclusion. Also, a drawback of this approach is that, in several cases, an incorrrectly spliced MyD88$_L$ isoform in which the intron between exon 2 and exon 3 is still present will be formed.

We use the following antisense oligo to prevent alternative splicing of human MyD88 to MyD88$_S$: 5'-GGCAUAUGCCCUGGGUGCAGA-3' (SEQ ID NO:9).

Alternatively, administration of antisense oligos designed against the intron-exon junction of the 3' acceptor splice site of exon 2, the balance may be tilted to favor exon2 exclusion and formation of MyD88$_S$.

We use the following antisense oligo to induce alternative splicing of human MyD88 to MyD88$_S$: 5'-GCAAUCCUC-CUCUGUGGGGAA-3'.

Alternatively, differential splicing of MyD88 can also be modulated by overexpression of specific splicing factors (e.g., SR proteins, hnRNP proteins; Chabot (1996) *Trends in Genetics* 12:472). A similar approach has been followed to modulate alternative splicing of CD45 by overexpression of specific SR proteins (ten Dam et al. (2000) *J. Immunol.* 164:5287).

Materials and Methods

Cell Culture and Biological Reagents

Cells were grown in RPMI 1640 (in case of mouse macrophage Mf4/4 and human monocyte THP-1 cells) or DMEM (in case of human embryonic kidney (HEK) 293T cells), supplemented with 10% fetal calf serum, 2 mM L-glutamine, 100 U/ml penicillin, 100 µg/ml streptomycin, 1 mM sodium pyruvate, and 50 µM 2-mercaptoethanol. Recombinant mouse TNF-α and IL-1β was provided by Apotech (San Diego, Calif., USA) and Sigma, respectively. Lipopolysaccharide (LPS) from *Salmonella abortus equi* was purchased from Sigma (Saint Louis, Mo., USA). The source of the various antibodies used in this study is as follows: anti-Flag/M2 (Eastman Kodak Company), anti-VSV (Sigma), anti-IRAK-1 (Alexis or Santa Cruz), anti-MyD88 (ProSci Incorporated) and anti-E (Pharmacia) antibodies.

PCR Amplification of MyD88

Total RNA was reverse transcribed with Superscript II RNase H⁻ reverse transcriptase (Gibco BRL, Life Technologies, Paisley, UK) and oligo (dT) primer. A Balb/c mouse multiple tissue cDNA panel was purchased from Clontech (Palo Alto, Calif., USA). The quality of the cDNA was verified by PCR amplification of β-actin. Primers, hybridizing to the 5'-end (5'-GGAATTCCCATGGGCGGCCGC-GATGTCTGCGGGAGACCCCCGC-3') (SEQ ID NO:11) and 3'-end (5'-cgccctgcagctcgagtcagggcaggga-caaagccttggcaag-3') (SEQ ID NO:12) of the open reading frame of murine MyD88 were used for PCR amplification of MyD88.

Expression Plasmids and Yeast 2-Hybrid Constructs pCAGGS-E-MyD88$_L$ and pCAGGS-E-MyD88$_S$ were obtained by in-frame cloning of RT-PCR fragments of MyD88 with an N-terminal E-tag into the eukaryotic expression vector pCAGGS. pCDNA3-AU1-MyD88-TIR (152–296) was a generous gift of Dr. M. Muzio (Mario Negri Institute, Milan) and was described in Muzio M. et al (1997) *Science* 278:1612. pPCRIII-Flag-MyD88, pPCRIII-Flag-IL1R, pPCRIII-Flag-IL1RAcP, pcDNA3-IRAK (T66A) and pcDNA3-IRAK-N(T66A) were described in Burns K. et al. (2000) *Nat. Cell Biol.* 2:346. pNFconluc, containing the luciferase reporter gene driven by a minimal NF-κB responsive promoter, was a gift of Dr. A. Israel (Institut Pasteur, Paris). pPGK-neogal, containing the β-galactosidase gene after the PGK promoter, was obtained from Dr. P. Soriano (Fred. Hutchinson Cancer Research Institute, Seattle). IRAK-4 was PCR amplified from an EST clone and inserted into pCRIII containing an N-terminal Flag or VSV tag or into pGAD10. Kinase dead mutants of IRAK-4 (IRAK-4KK213AA or IRAK-4D311N) were generated by double PCR and inserted into a pCRIII vector with an N-terminal tag. pGBT9 MyD88, pGBT9 MyD88-N (aa 1–172), pGBT9 MyD88-TIR (aa 161–296), expressing pGALDB (the GAL4 DNA-binding domain) fused to full-length MyD88 or the indicated deletion mutants have been described previously (Burns et al. (1998) *J. Biol. Chem.* 273: 12203–12209). pGBT9 MyD88-ID (aa 110–157) and pGBT9 MyD88-DD (aa 1–110) were prepared by inserting PCR-generated fragments into pGBT9. The sequence of all PCR-generated cDNAs were confirmed by DNA sequencing. pGAD10 IRAK-4 expressing Gal4AD-IRAK4 (a fusion protein of GAL4 transcription activation with full-length IRAK-4) was made by inserting IRAK-4 cDNA as an EcoRI fragment into pGAD10. An AP-1-dependent luciferase reporter construct, pAP-1luc, was purchased from Stratagene (PathDetect System).

Transient Transfections and NF-κB or AP-1 Reporter Gene Assays

HEK 293T cells were seeded in 6-well plates at 2×10⁵ cells/well and transiently transfected by the DNA-calcium phosphate precipitation method with 100 ng pNFconluc or 100 ng pAP-1luc, 100 ng pGK-neogal and different concentrations of specific MyD88 expression plasmids. The total amount of DNA was kept constant by adding empty vector up to 1 µg DNA per well. Transfections were done in triplicate. Six hours post-transfection, cells were trypsinized and seeded at a density of 2×10⁴ cells/well in 24-well plates. 3×10⁶ Mf4/4 cells were transiently transfected by electroporation (conditions: 300 V and 1350 µF) with 1 µg pPGK-neogal, 4 µg pNFconluc and 5 µg of a MyD88 expression plasmid. Transfected cells were seeded at a density of 2.5×10⁵ c/well in a 24-well plate. 48 hours post-transfection cells were stimulated for 6 hours with 100 ng/ml IL1-β, 100 ng/ml TNF, 100 ng/ml LPS or left untreated. NF-κB and AP-1 activity was determined by measuring the luciferase activity present in cell extracts. Luciferase values were normalized for differences in transfection efficiency on the basis of β-galactosidase activity in the same extracts, and expressed as fold induction values relative to the unstimulated empty vector control.

Gel Retardation Assays

HEK 293T cells were seeded at 1.5×10⁶ cells/10 cm petri dish and transfected with pCAGGS-E-MyD88$_S$, pCAGGS-E-MyD88$_L$ or empty vector. Nuclear fractions were prepared as described by Dignam J. D. et al. (1983) *Nucleic Acid Res.* 11:1475. NF-κB DNA-binding activity was analyzed by incubating 8 µg nuclear proteins for 30 minutes with the 32P-end-labeled oligonucleotide 5'-agctATGTGG-GATTTTCCCATGGAGCagct-3' (SEQ ID NO:13), corresponding to the NF-κB recognition sequence of the Ig κB promoter. DNA/nucleoprotein complexes were separated from free probe on a 4% polyacrylamide gel.

Co-Immunoprecipitation and Western Blotting

2×10⁶ HEK293T cells were plated on 10-cm petri dishes and transiently transfected with 1 µg of the indicated expression plasmids. The total amount of DNA was kept at 5 µg per petri dish by adding empty vector. Twenty-four hours post-transfection, cells were washed with PBS, and lysed in 500 µl lysis buffer (50 mM HEPES pH7.6, 250 mM NaCl, 0.1% NP-40, 5 mM EDTA, supplemented with protease and phosphatase inhibitors). Lysates were incubated for 16 hours with 5 µg anti-Flag (Sigma). Immunocomplexes were immobilized on protein A-Trisacryl beads (Pierce Chemical Co., Rockford, USA). The beads were washed twice with lysis buffer and twice with lysis buffer containing 1 M NaCl. Bound proteins were eluted by boiling in Laemli buffer and analyzed by 10% SDS-PAGE and Western blotting. Western blots were blocked with 5% milk and incubated overnight with primary antibodies. Antibodies raised against the C-terminal part of MyD88 were purchased from Immucor (Roedermark, Germany). An E-tag antibody was purchased from Amersham Pharmacia Biotech (Rainham, UK), an IRAK-antibody from Alexis (San Diego, Calif., USA) and an IκB-α antibody from Santa Cruz Biotechnology Inc. (Santa Cruz, Calif., USA). HRP-conjugated anti-mouse or HRP-conjugated anti-rabbit secondary antibodies were purchased from Amersham Pharmacia Biotech and incubated with the blots for 1 hour. Immunoreactive bands were revealed by enhanced chemiluminescence (ECL, Amersham Pharmacia Biotech). For detection of JNK phosphorylation, cell lysates were prepared in RIPA buffer (25 mM Tris pH8.2, 50 mM NaCl, 0.5% NP-40, 0.5% deoxycholic acid, 0.1% SDS, 10 μM iodoacetate), supplemented with protease and phosphatase inhibitors. Lysates were analyzed by 10% SDS-PAGE and Western blotting with anti-JNK or anti-phospoJNK (Cell Signaling, Beverly, Mass., USA).

TNF Bio-Assay

TNF levels in the supernatants of THP-1 cells were measured in a bioassay for TNF which is based on TNF cytotoxicity for the mouse fibroblast cell line L929 in the presence of 1 μg/ml actinomycin D, as described in Schotte P. et al (2001) *J. Biol. Chem.* 276: 25939.

Yeast 2-Hybrid Interaction Studies.

Interaction of full-length IRAK-4 with different deletion mutants of MyD88 was evaluated by yeast-two-hybrid interaction studies, performed as described previously (De Valck et al. (1996) *FEBS Lett.* 384: 61–64. Briefly, yeast cells of the *S. cerevisiae* strain HF7c were co-transformed with the pGAD10 IRAK-4 and pGBT9 MyD88 or pGBT9 fused to different MyD88 deletion mutants. Transformation efficiency was verified by growth on appropriate synthetic media using Trp and Leu selection markers. Protein interaction was revealed by His auxotrophy and assessed by b-galactosidase expression filter assays. All pGBT9 MyD88 fusion proteins were negative for autoactivation.

Immunoprecipitation and Kinase Assays.

Transfected 293T cells were lysed in lysis buffer (1% NP-40, 20 mM HEPES, pH 7.9, 250 mM NaCl, 20 mM b-glycerophosphate, 10 mM NaF, 1 mM sodium orthovanadate, 2 mM dithiothreitol, 1 mM EDTA and a protease inhibitor cocktail). Following lysis, the cell extracts were incubated with one of the following antibodies for 2 hours at 4° C.: (1 μg) anti-M2, anti-VSV, anti-IRAK-1, or anti-E that were preincubated with protein G Sepharose. After incubation, the beads were washed six times with lysis buffer, separated by SDS-PAGE, transferred to Nitrocellulose and analyzed by immunoblotting. For the kinase assays, transiently transfected HEK 293T cells were lysed in 500 μl of 20 mM Tris pH 7.5, 50 mM KCl, 5 mM MgCl2, 400 mM NaCl, 2 mM DTT, 1% Triton-X-100, 20% glycerol and protease and phosphatase inhibitors. IRAK-1KD was immunoprecipitated for 2 hours at 4° C. with an anti-IRAK-1 antibody (Alexis), followed by addition of protein A trisacryl (Pierce). Immune complexes were washed twice with lysis buffer and twice with kinase buffer containing 20 mM Tris-HCl, pH 7.5, 50 mM KCl, 2 mM MgCl2, 2 mM MnCl2, 5% glycerol and protease inhibitors. After the last wash, immune complexes were resuspended in 40 μl kinase buffer. For each kinase reaction, 10 ml of the respective immune complexes were mixed with 5 μCi of gamma-$^{32}$P] ATP (3000 Ci/mmol) in total volume of 25 μl. Reactions were allowed to proceed for 15 minutes at 30° C. and then directly analyzed by SDS-PAGE and autoradiography. A reaction without ATP added was set up in parallel and analyzed by western blot to estimate the input.

REFERENCES

1. Wesche H., Henzel W. J., Shillinglaw W., Li S., Cao Z. MyD88: an adapter that recruits IRAK to the IL-1 receptor complex. *Immunity* 1997, 7:837–847.
2. Medzhitov R., Preston-Hurlburt P., Kopp E., Stadlen A., Chen C., Ghosh S., Janeway C. Jr. MyD88 is an adaptor protein in the hToll/IL-1 receptor family signaling pathways. *Mol. Cell.* 1998, 2:253–258.
3. Burns K., Martinon F., Esslinger C., Pahl H., Schneider P., Bodmer J.-L., Di Marco F., French L., Tschopp J. MyD88, an adaptor protein involved in interleukin-1 signaling. *J. Biol. Chem.* 1998, 273:12203–12209.
4. Burns K., Clatworthy J., Martin L., Martinon F., Plumpton C., Maschera B., Lewis A., Ray K., Tschopp J., Volpe F. Tollip, a new component of the IL1 pathway, links IRAK to the IL1 receptor. *Nat. Cell. Biol.* 2000, 2:346–351.
5. Li X., Commane M., Jiang Z., Stark, G. R. IL-1-induced NFκB and c-Jun N-terminal kinase (JNK) activation diverge at IL-1 receptor-associated kinase (IRAK). *Proc. Natl. Acad. Sci. USA* 2001, 98:4461–4465.
6. Hardiman G., Jenkins N. A., Copeland N. G., Gilbert D. J., Garcia D. K., Naylor S. L., Kastelein R. A., Bazan J. F. Genetic structure and chromosomal mapping of MyD88. *Genomics* 1997, 45:332–340.
7. Lord K. A., Hoffman-Liebermann B., Liebermann D. A. Nucleotide sequence and expression of a cDNA encoding MyD88, a novel myeloid differentiation primary response gene induced by IL6. *Oncogene* 1990, 5:1095–1101.
8. Adachi O., Kawai T., Takeda K., Matsumoto M., Tsutsui H., Sakagami M., Nakanishi K., Akira S. Targeted disruption of the MyD88 gene results in loss of IL-1- and IL-1 8-mediated function. *Immunity* 1998, 9:143–150.
9. Lomaga M. A., Yeh W. C., Sarosi I., Duncan G. S., Furlonger C., Ho A., Morony S., Capparelli C., Van G., Kaufman S., van der Heiden A., Itie A., Wakeham A., Khoo W., Sasaki T., Cao Z., Penninger J. M., Paige C. J., Lacey D. L., Dunstan C. R., Boyle W. J., Goeddel D. V., Mak T. W. TRAF6 deficiency results in osteopetrosis and defective interleukin-1, CD40, and LPS signaling. *Genes Dev.* 1999, 13:1015–1024.
10. Cao Z., Henzel W. J., Gao X. IRAK: a kinase associated with the interleukin-1 receptor. *Science* 1996, 271:1128–1131.
11. Li X., Commane M., Burns C., Vithalani K., Cao Z., Stark G. R. Mutant cells that do not respond to interleukin-1 (IL-1) reveal a novel role for IL-1 receptor associated kinase. *Mol. Cell. Biol.* 1999, 19:4643–4652.
12. Cao Z., Ziong J., Takeuchi M., Kurama T., Goeddel D. V. TRAF6 is a signal transducer for interleukin-1. *Nature* 1996b, 383:443–446.
13. Kawai T., Adachi O., Ogawa T., Takeda K., Akira S. Unresponsiveness of MyD88-deficient mice to endotoxin. *Immunity* 1999, 11:115–122.
14. Henneke P., Golenbock D. T. TIRAP: how Toll receptors fraternize. *Nature Immunol.* 2001, 2:828–830.
15. Ziegler-Heitbrock H. W. L., Frankenberger M., Wedel A. Tolerance to lipopolysaccharide in human blood monocytes. *Immunobiol.* 1995, 193:217–223.
16. Nomura F., Akashi S., Sakao Y., Sato S., Kawai T., Matsumoto M., Nakanishi K., Kimoto M., Miyake K., Takeda K., Akira S. Cutting edge: Endotoxin tolerance in mouse peritoneal macrophages correlates with downregulation of surface toll-like receptor 4 expression. *J. Immunol.* 2000, 164:3476–3479.
17. Li L., Cousart S., Hu J., McCall C. E. Characterization of interleukin-1 receptor-associated kinase in normal and endotoxin-tolerant cells. *J. Biol. Chem.* 2000 275:23340–23345.

What is claimed is:

1. An isolated polynucleotide which encodes a polypeptide comprising amino acids 1–251 of SEQ ID NO:2 wherein the codons encoding amino acids 1–251 are contiguous and possessing the biological properties of (a) down regulating TLR induced nuclear factor Kappa β activation, and (b) activating c-JUN-terminal kinase pathway.

2. The polynucleotide of claim 1 as set forth in SEQ ID NO:1.

3. The polynucleotide of claim 1, wherein said TLR functions as a receptor for LPS.

4. An isolated polynucleotide encoding a peptide comprising a variant of $MyD_{88}$ lacking the domain between the N-terminal death domain and the C-terminal TIR domain, the peptide inhibiting LPS-induced NF-kb activation and possessing the biological properties of (a) down regulating TLR induced nuclear factor kappa B activation, and (b) activating c JUN N terminal kinase pathway.

* * * * *

UNITED STATES PATENT AND TRADEMARK OFFICE
CERTIFICATE OF CORRECTION

PATENT NO. : 7,122,656 B2  
APPLICATION NO. : 10/888288  
DATED : October 17, 2006  
INVENTOR(S) : Rudi Beyaert and Sophie Janssens Page 1 of 1

It is certified that error appears in the above-identified patent and that said Letters Patent is hereby corrected as shown below:

In the specification:

COLUMN 12, LINE 36, change "intemucleoside" to --internucleoside--  
COLUMN 29, LINE 10, at the end of the line add "(SEQ ID NO: 10)"

In the claims:

CLAIM 1, COLUMN 41, LINE 37, change "Kappa β activation," to --kappa β activation,--  
CLAIM 1, COLUMN 41, LINE 38, change "c-JUN-terminal kinase pathway." to --c-JUN N-terminal kinase pathway.--

Signed and Sealed this

Seventh Day of July, 2009

JOHN DOLL  
*Acting Director of the United States Patent and Trademark Office*

SEQUENCE LISTING

<160> NUMBER OF SEQ ID NOS: 15

<210> SEQ ID NO 1
<211> LENGTH: 756
<212> TYPE: DNA
<213> ORGANISM: Homo sapiens

<400> SEQUENCE: 1

```
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca gcggaccccc actggcaggc tgctggacgc ctggcaggga     240
cgccctggcg cctctgtagg ccgactgctc gagctgctta ccaagctggg ctgcgacgac     300
gtgctgctgg agctgggacc cagcattggg catatgcctg agcgtttcga tgccttcatc     360
tgctattgcc ccagcgacat ccagtttgtg caggagatga tccggcaact ggaacagaca     420
aactatcgac tgaagttgtg tgtgtctgac cgcgatgtcc tgcctggcac ctgtgtctgg     480
tctattgcta gtgagctcat cgaaaagagg tgccgccgga tggtggtggt tgtctctgat     540
gattacctgc agagcaagga atgtgacttc agaccaaat ttgcactcag cctctctcca     600
ggtgcccatc agaagcgact gatccccatc aagtacaagg caatgaagaa agagttcccc     660
agcatcctga ggttcatcac tgtctgcgac tacaccaacc cctgcaccaa atcttggttc     720
tggactcgcc ttgccaaggc cttgtccctg ccctga                              756
```

<210> SEQ ID NO 2
<211> LENGTH: 251
<212> TYPE: PRT
<213> ORGANISM: Homo sapiens

<400> SEQUENCE: 2

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Gly His Met
            100                 105                 110

Pro Glu Arg Phe Asp Ala Phe Ile Cys Tyr Cys Pro Ser Asp Ile Gln
        115                 120                 125

Phe Val Gln Glu Met Ile Arg Gln Leu Glu Gln Thr Asn Tyr Arg Leu
    130                 135                 140

Lys Leu Cys Val Ser Asp Arg Asp Val Leu Pro Gly Thr Cys Val Trp
145                 150                 155                 160

Ser Ile Ala Ser Glu Leu Ile Glu Lys Arg Cys Arg Arg Met Val Val
                165                 170                 175
```

```
Val Val Ser Asp Asp Tyr Leu Gln Ser Lys Glu Cys Asp Phe Gln Thr
            180                 185                 190

Lys Phe Ala Leu Ser Leu Ser Pro Gly Ala His Gln Lys Arg Leu Ile
        195                 200                 205

Pro Ile Lys Tyr Lys Ala Met Lys Lys Glu Phe Pro Ser Ile Leu Arg
    210                 215                 220

Phe Ile Thr Val Cys Asp Tyr Thr Asn Pro Cys Thr Lys Ser Trp Phe
225                 230                 235                 240

Trp Thr Arg Leu Ala Lys Ala Leu Ser Leu Pro
                245                 250
```

<210> SEQ ID NO 3
<211> LENGTH: 756
<212> TYPE: DNA
<213> ORGANISM: Mus musculus

<400> SEQUENCE: 3

```
atgtctgcgg gagacccccg cgtgggatcc gggtccctgg actccttcat gttctccata    60
cccttggtcg cgcttaacgt gggagtgagg cgccgcctat cgctgttctt gaaccctcgg   120
acgcccgtgg cggccgactg gaccttgctc ccggaggaga tgggcttcga gtacttggag   180
atccgagagc tggaaacgcg ccctgacccc actcgcagtt tgttggatgc ctggcagggg   240
cgctctggcg cgtctgtcgg caggctgcta gagctgctgg ccttgttaga ccgtgaggat   300
atactgaagg agctgaagtc gcgcatcgga caaacgccgg aacttttcga tgcctttatc   360
tgctactgcc ccaacgatat cgagtttgtg caggagatga tccggcaact agaacagaca   420
gactatcggc ttaagttgtg tgtgtccgac cgtgacgtcc tgccgggcac ctgtgtctgg   480
tccattgcca gcgagctaat tgagaaaagg tgtcgccgca tggtggtggt tgtttctgac   540
gattatctac agagcaagga atgtgacttc cagaccaagt ttgcactcag cctgtctcca   600
ggtgtccaac agaagcgact gattcctatt aaatacaagg cgatgaagaa ggactttccc   660
agtatcctgc ggttcatcac tatatgcgac tataccaacc cttgcaccaa gtcctggttc   720
tggacccgcc ttgccaaggc tttgtccctg ccctga                             756
```

<210> SEQ ID NO 4
<211> LENGTH: 251
<212> TYPE: PRT
<213> ORGANISM: Mus musculus

<400> SEQUENCE: 4

```
Met Ser Ala Gly Asp Pro Arg Val Gly Ser Gly Ser Leu Asp Ser Phe
1               5                   10                  15

Met Phe Ser Ile Pro Leu Val Ala Leu Asn Val Gly Val Arg Arg Arg
            20                  25                  30

Leu Ser Leu Phe Leu Asn Pro Arg Thr Pro Val Ala Ala Asp Trp Thr
        35                  40                  45

Leu Leu Pro Glu Glu Met Gly Phe Glu Tyr Leu Glu Ile Arg Glu Leu
    50                  55                  60

Glu Thr Arg Pro Asp Pro Thr Arg Ser Leu Leu Asp Ala Trp Gln Gly
65                  70                  75                  80

Arg Ser Gly Ala Ser Val Gly Arg Leu Leu Glu Leu Leu Ala Leu Leu
                85                  90                  95

Asp Arg Glu Asp Ile Leu Lys Glu Leu Lys Ser Arg Ile Gly Gln Thr
            100                 105                 110
```

-continued

```
Pro Glu Leu Phe Asp Ala Phe Ile Cys Tyr Cys Pro Asn Asp Ile Glu
    115                 120                 125
Phe Val Gln Glu Met Ile Arg Gln Leu Glu Gln Thr Asp Tyr Arg Leu
    130                 135                 140
Lys Leu Cys Val Ser Asp Arg Asp Val Leu Pro Gly Thr Cys Val Trp
145                 150                 155                 160
Ser Ile Ala Ser Glu Leu Ile Glu Lys Arg Cys Arg Met Val Val
                165                 170                 175
Val Val Ser Asp Asp Tyr Leu Gln Ser Lys Glu Cys Asp Phe Gln Thr
            180                 185                 190
Lys Phe Ala Leu Ser Leu Ser Pro Gly Val Gln Gln Lys Arg Leu Ile
        195                 200                 205
Pro Ile Lys Tyr Lys Ala Met Lys Lys Asp Phe Pro Ser Ile Leu Arg
    210                 215                 220
Phe Ile Thr Ile Cys Asp Tyr Thr Asn Pro Cys Thr Lys Ser Trp Phe
225                 230                 235                 240
Trp Thr Arg Leu Ala Lys Ala Leu Ser Leu Pro
                245                 250
```

```
<210> SEQ ID NO 5
<211> LENGTH: 23
<212> TYPE: DNA
<213> ORGANISM: Artificial Sequence
<220> FEATURE:
<223> OTHER INFORMATION: sequence used to knock down MyD88L - murine
      MyD88

<400> SEQUENCE: 5
aaccaggagt ccgagaagcc ttt                                            23

<210> SEQ ID NO 6
<211> LENGTH: 22
<212> TYPE: DNA
<213> ORGANISM: Artificial Sequence
<220> FEATURE:
<223> OTHER INFORMATION: sequence used to knock down MyD88L - human
      MyD88

<400> SEQUENCE: 6
aagcctttac aggtggccgc tg                                             22

<210> SEQ ID NO 7
<211> LENGTH: 21
<212> TYPE: DNA
<213> ORGANISM: Artificial Sequence
<220> FEATURE:
<223> OTHER INFORMATION: sequence used to knock down MyD88s - murine
      MyD88

<400> SEQUENCE: 7
aagtcgcgca tcggacaaac g                                              21

<210> SEQ ID NO 8
<211> LENGTH: 21
<212> TYPE: DNA
<213> ORGANISM: Artificial Sequence
<220> FEATURE:
<223> OTHER INFORMATION: sequence used to knock down MyD88s - human
      MyD88
```

```
<400> SEQUENCE: 8
cattgggcat atgcctgagc g                                              21

<210> SEQ ID NO 9
<211> LENGTH: 21
<212> TYPE: RNA
<213> ORGANISM: Artificial Sequence
<220> FEATURE:
<223> OTHER INFORMATION: antisense oligo used to prevent alternative
      splicing of human MyD88 to MyD88s

<400> SEQUENCE: 9
ggcauaugcc cugggugcag a                                              21

<210> SEQ ID NO 10
<211> LENGTH: 21
<212> TYPE: RNA
<213> ORGANISM: Artificial Sequence
<220> FEATURE:
<223> OTHER INFORMATION: antisense oligo used for inducing alternative
      splicing of human MyD88 to MyD88s

<400> SEQUENCE: 10
gcaauccucc ucugugggga a                                              21

<210> SEQ ID NO 11
<211> LENGTH: 43
<212> TYPE: DNA
<213> ORGANISM: Artificial Sequence
<220> FEATURE:
<223> OTHER INFORMATION: primer hybridizing to the 5'-end of the ORF of
      murine MyD88 used for PCR amplification of MyD88

<400> SEQUENCE: 11
ggaattccca tgggcggccg cgatgtctgc gggagacccc cgc                      43

<210> SEQ ID NO 12
<211> LENGTH: 43
<212> TYPE: DNA
<213> ORGANISM: Artificial Sequence
<220> FEATURE:
<223> OTHER INFORMATION: primer hybridizing to the 3'-end of the ORF of
      murine MyD88 used for PCR amplification of MyD88

<400> SEQUENCE: 12
cgccctgcag ctcgagtcag ggcagggaca aagccttggc aag                      43

<210> SEQ ID NO 13
<211> LENGTH: 30
<212> TYPE: DNA
<213> ORGANISM: Artificial Sequence
<220> FEATURE:
<223> OTHER INFORMATION: 32-P-end-labeled oligonucleotide

<400> SEQUENCE: 13
agctatgtgg gattttccca tggagcagct                                     30

<210> SEQ ID NO 14
<211> LENGTH: 77
<212> TYPE: PRT
<213> ORGANISM: Homo sapiens
```

```
-continued

<400> SEQUENCE: 14

Leu Gly Arg Asp Asp Val Leu Leu Glu Leu Gly Pro Ser Ile Glu Glu
1               5                   10                  15

Asp Cys Gln Lys Tyr Ile Leu Lys Gln Gln Gln Glu Glu Ala Glu Lys
            20                  25                  30

Pro Leu Gln Val Ala Ala Val Asp Ser Ser Val Pro Arg Thr Ala Glu
        35                  40                  45

Leu Ala Gly Ile Thr Thr Leu Asp Asp Pro Leu Gly His Met Pro Glu
    50                  55                  60

Arg Phe Asp Ala Phe Ile Cys Tyr Cys Pro Ser Asp Ile
65                  70                  75

<210> SEQ ID NO 15
<211> LENGTH: 44
<212> TYPE: PRT
<213> ORGANISM: Homo sapiens

<400> SEQUENCE: 15

Glu Asp Cys Gln Lys Tyr Ile Leu Lys Gln Gln Gln Glu Glu Ala Glu
1               5                   10                  15

Lys Pro Leu Gln Val Ala Ala Val Asp Ser Ser Val Pro Arg Thr Ala
            20                  25                  30

Glu Leu Ala Gly Ile Thr Thr Leu Asp Asp Pro Leu
        35                  40
```